(12) United States Patent
Bix et al.

(10) Patent No.: US 9,358,273 B2
(45) Date of Patent: Jun. 7, 2016

(54) USE OF PERLECAN DOMAIN V IN TREATING AMYLOIDOGENIC DISEASE

(75) Inventors: Gregory J. Bix, College Station, TX (US); Sarah Wright, San Francisco, CA (US); Irene Griswold-Prenner, San Francisco, CA (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 63 days.

(21) Appl. No.: 13/519,949

(22) PCT Filed: Jan. 6, 2011

(86) PCT No.: PCT/US2011/020426
§ 371 (c)(1),
(2), (4) Date: Oct. 16, 2012

(87) PCT Pub. No.: WO2011/085136
PCT Pub. Date: Jul. 14, 2011

(65) Prior Publication Data
US 2013/0036481 A1 Feb. 7, 2013

Related U.S. Application Data

(60) Provisional application No. 61/292,803, filed on Jan. 6, 2010.

(51) Int. Cl.
*A61K 38/39* (2006.01)
(52) U.S. Cl.
CPC ...................................... *A61K 38/39* (2013.01)
(58) Field of Classification Search
None
See application file for complete search history.

(56) References Cited

U.S. PATENT DOCUMENTS

| 7,488,719 | B1  | 2/2009 | DeCarlo et al. |       |
|-----------|-----|--------|----------------|-------|
| 7,510,843 | B2  | 3/2009 | Roecklin et al. |      |
| 2003/0104999 | A1 | 6/2003 | Iozzo |            |
| 2003/0109435 | A1* | 6/2003 | Prenner et al. | 514/12 |
| 2003/0153734 | A1 | 8/2003 | Castillo et al. |      |
| 2007/0128190 | A1 | 6/2007 | Lazarides et al. |     |
| 2008/0193444 | A1 | 8/2008 | Wright et al. |       |
| 2009/0220505 | A1 | 9/2009 | Griswold-Prenner et al. | |
| 2010/0168025 | A1 | 7/2010 | Bix |                |
| 2012/0003180 | A1 | 1/2012 | Bix |                |

FOREIGN PATENT DOCUMENTS

| WO | WO 98/39653    | * | 9/1998 | ............. G01N 33/53 |
| WO | WO 2010/077364 |   | 7/2010 |                          |
| WO | WO 2012/003452 |   | 1/2012 |                          |

OTHER PUBLICATIONS

Wells, 1990, Biochemistry 29:8509-8517.*
Ngo et al., 1994, The Protein Folding Problem and Tertiary Structure Prediction, pp. 492-495.*
Tokuriki and Tawfik, Current Opinion in Structural Biology 2009, 19: 596-604.*
Murdoch et al., J Biol Chem, 1992; 267: 8544-8557.*
Cao et al., J Neurosci, 2002; 22: 5423-5431.*
Bix, G. et al. "Endorepellin causes endothelial cell disassembly of actin cytoskeleton and focal adhesions through α2β1 intergrin" *The Journal of Cell Biology*, Jul. 5, 2004, pp. 97-109, vol. 166, No. 1.
Bix, G. et al. "Endorepellin, the C-terminal angiostatic module of perlecan, enhances collagen-platelet response via the α2β1-intergrin receptor" *Blood*, May 1, 2007, pp. 3745-3748, vol. 109, No. 9.
Bix, G. et al. "Endorepellin In Vivo: Targeting the Tumor Vasculature and Retarding Cancer Growth and Metabolism" *Journal of the National Cancer Institute*, Nov. 15, 2006, pp. 1634-1646, vol. 98, No. 22.
Bix, G. et al. "Novel Interactions of Perlecan: Unraveling Perlecan's Role in Angiogenesis" *Microscopy Research and Technique*, 2008, pp. 339-348, vol. 71.
Adams, S. L. "Collagen Gene Expression" *American Journal of Respiratory Cell and Molecular Biology*, 1989, pp. 161-168, vol. 1.
Beckmann, G. et al. "Merging Extracellular Domains: Fold Prediction for Laminin G-like and Amino-terminal Thrombospondin-like Modules Based on Homology to Pentraxins" *J. Mol. Biol.*, 1998, pp. 725-730, vol. 275.
Castillo, G. M. et al. "Laminin Inhibition of β-Amyloid Protein (Aβ) Fibrillogenesis and Identification of an Aβ Binding Site Localized to the Globular Domain Repeats on the Laminin A Chain" *Journal of Neuroscience Research*, 2000, pp. 451-462, Vo. 62.
Murtomaki, S. et al. "Laminin and Its Neurite Outgrowth-Promoting Domain in the Brain in Alzheimer's Disease and Down's Syndrome Patients" *Journal of Neuroscience Research*, 1992, pp. 261-273, vol. 32.
Bronfman, F.C. et al. "Laminin blocks the assembly of wild-type A beta and the Dutch variant peptide into Alzheimer's fibrils" *Amyloid*, Mar. 1998, p. 1, vol. 1, No. 1, abstract only.
Wright, S., et al., "Perlecan domain V inhibits α2 integrin-mediated amyloid-β neurotoxicity," *Neurobiology of Aging*, 2012, vol. 33, No. 7, pp. 1379-1388.

* cited by examiner

*Primary Examiner* — Christina Borgeest
(74) *Attorney, Agent, or Firm* — Saliwanchik, Lloyd & Eisenschenk

(57) ABSTRACT

The application reports that perlecan domain V (DV) or the LG3 domain thereof reduces deposition and toxicity of Aβ peptide, the major component of plaques in Alzheimer's disease. Methods of using DV, LG3 and related molecules in treatment of amyloidogenic diseases, particularly Alzheimer's disease, are provided.

26 Claims, 12 Drawing Sheets
(9 of 12 Drawing Sheet(s) Filed in Color)

FIG. 2A  α2β1 Null Vector Control Cells
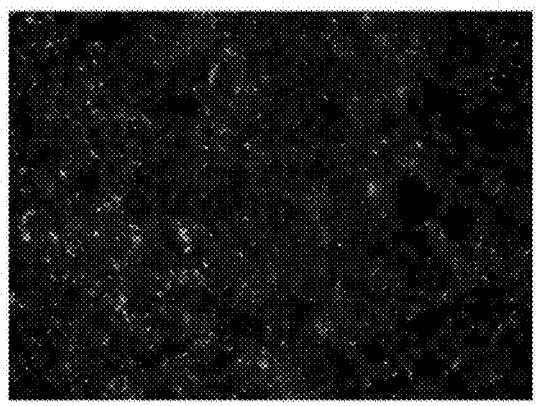
α2β1 Wild Type Cells
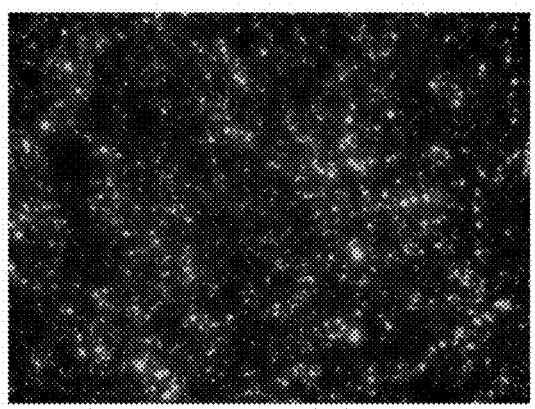
α2β1 Activation Mutant Cells
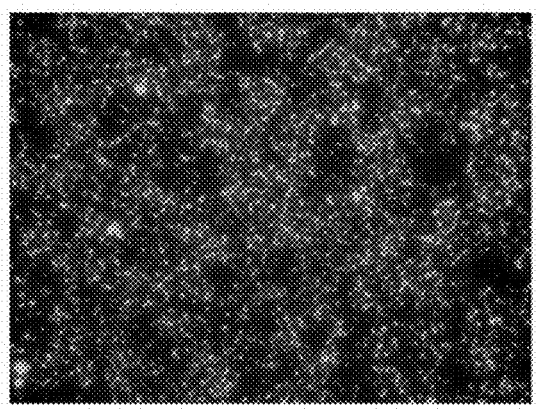
FIG. 2B
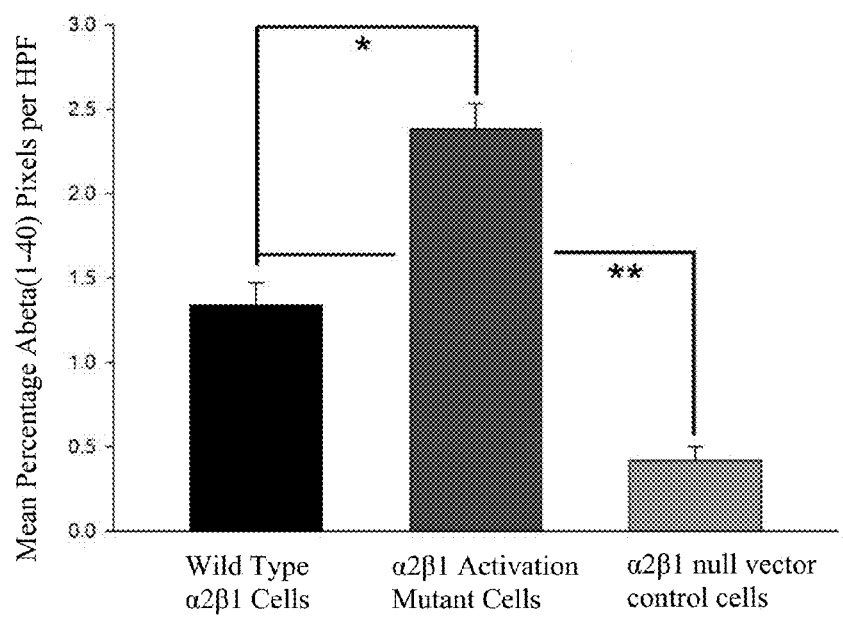

1 Control
2 Control + AB1-40 7 uM
3 Control + AB1-40 15uM
4 Control + AB1-40 30uM
5 Control+AB1-40+Alphav Ig 267 nM
6 Alpha2 null Control
7 Alpha2 null +AB1-40 7 uM
8 Alpha2 null+AB1-40 15 uM
9 Alpha2 null+AB1-40 30 uM
10 Alpha2 null+AB1-40 30uM+Alphav Ig 267 nM

```
       3670       3680       3690       3700       3710       3720
VPYFTQTP YSFLPLPTIK DAYRKFEIKI TFRPDSADGM LLYNGQKRVP GSPTNLANRQ 3730       3740       3750       3760       3770       3780
PDFISFGLVG GRPEFRFDAG SGMATIRHPT PLALGHFETV TLLRSLTQGS LIVGDLAPVN 3790       3800       3810       3820       3830       3840
GTSQGKFQGL DLNEELYLGG YPDYGAIPKA GLSSGFIGCV RELRIQGEEI VFHDLNLTAH 3850       3860       3870       3880       3890       3900
GISHCPTCRD RPCQNGGQCH DSESSSYVCV CPAGFTGSRC EHSQALHCHP EACGPDATCV 3910       3920       3930       3940       3950       3960
NRPDGRGYTC RCHLGRSGLR CEEGVTVTTP SLSGAGSYLA LPALTNTHHE LRLDVEFKPL 3970       3980       3990       4000       4010       4020
APDGVLLFSG GKSGPVEDFV SLAMVGGHLE FRYELGSGLA VLRSAEPLAL GRWHRVSAER 4030       4040       4050       4060       4070       4080
LNKDGSLRVN GGRPVLRSSP GKSQGLNLHT LLYLGGVEPS VPLSPATNMS AHFRGCVGEV 4090       4100       4110       4120       4130       4140
SVNGKRLDLT YSFLGSQGIG QCYDSSPCER QPCQHGATCM PAGEYEFQCL CRDGFKGDLC 4150       4160       4170       4180       4190       4200
EHEENPCQLR EPCLHGGTCQ GTRCLCLPGF SGPRCQQGSG HGIAESDWHL EGSGCNDAPG 4210       4220       4230       4240       4250       4260
QYGAYFHDDG FLAFPGHVFS RSLPEVPETI ELEVRTSTAS GLLLWQGVEV GEAGQGKDFI 4270       4280       4290       4300       4310       4320
SLGLQDGHLV FRYQLGSGEA RLVSEDPIND GEWHRVTALR EGRRGSIQVD GEELVSGRSP 4330       4340       4350       4360       4370       4380
GPNVAVNAKG SVYIGGAPDV ATLTGGRFSS GITGCVKNLV LHSARPGAFP PQPLDLQHRA

4390
QAGANTRPCP S
```

USE OF PERLECAN DOMAIN V IN TREATING AMYLOIDOGENIC DISEASE

CROSS-REFERENCE TO RELATED APPLICATIONS

This application is the U.S. national stage application of International Patent Application No. PCT/US2011/020426, filed Jan. 6, 2011, which claims the benefit of U.S. Application No. 61/292,803 filed Jan. 6, 2010, the contents of which are incorporated herein in their entirety for all purposes.

BACKGROUND OF THE INVENTION

The loss of cells and profound brain atrophy in Alzheimer's disease contributes to many of the clinical features of the disease. Initial synaptic toxicity followed by overt cell death has been proposed as a mechanism (Delaere et al., Acta Neuropathol. 77.6 (1989): 645-53). Aβ peptide, the primary component of the AD plaque, has been proposed to play a role in both synaptic and overt cell toxicity. Soluble Aβ rather than plaque-associated Aβ has been reported to correlate with loss of the synaptic protein synaptophysin (Lue et al., Am. J. Pathol. 155.3 (1999): 853-62). Non fibrillar forms of Aβ have been reported to have some synaptotoxic (Wang et al., J. Neurosci. 24.13 (2004): 3370-78; Lacor et al., 24.45 (2004): 10191-200) or overt toxic effects in cultures (Kim et al., FASEB J. 17.1 (2003): 118-20).

Aβ neurotoxicity can be analyzed by a polymerization-dependent toxicity assay (Wogulis et al., J. Neurosci. 25.5 (2005): 1071-80) in which soluble and fibrillar Aβ are combined to allow aggregation. If the aggregation occurs in or on a cell membrane, robust toxicity and deposition occurs. Specific integrin heterodimers mediating deposition, overt toxicity and synaptic toxicity of Aβ effects on LTP have been reported (Wright et al., Neurobiol. Aging 28.2 (2007): 226-37; Wang et al., Neurobiol. Aging 29.10 (2008): 1485-93).

Perlecan is a heparin sulfate proteoglycan that can be subdivided into five domains. Domain V (DV) also known as endorepellin is an 85-kDa C-terminal domain of perlecan. DV consists of three laminin globular (LG) domains, each separated by two epidermal growth factor (EGF)-like domains. The C-terminal most LG domain, known as LG3, is specifically processed from full length perlecan by the BMP-1 family of tolloid metalloproteases (Gonzalez et al., J. Biol. Chem. 280.8 (2005): 7080-87) and the cysteine proteinase cathepsin L (Cailhier et al., Journal of Biological Chemistry 283.40 (2008): 27220-29), and is normally found in the human urinary, blood and cerebrospinal fluid proteomes (Pieper et al., Proteomics. 4.4 (2004): 1159-74; Adkins et al. Mol. Cell Proteomics 1.12 (2002): 947-55; Cartier et al., Scand. J. Clin. Lab Invest 64.2 (2004): 101-07). Perlecan has been reported to have a role in cell growth, differentiation, brain and cardiovascular development, and inflammation (Bix & Iozzo, Microsc. Res. Tech. 71.5 (2008): 339-48). Domain V and LG3, a proteolytic fragment, have been reported to inhibit angiogenesis in endothelial cells in vitro and in vivo via direct interaction with the ligand-binding domain (I domain) of α2 integrin, (Bix et al., J. Cell. Biol. 166.1 (2004): 97-109; Bix et al., J. Natl. Cancer Inst. 98.22 (2006): 1634-46, U.S. Pat. No. 6,821,947). Perlecan has also been proposed to have a role in wound healing (see U.S. Pat. No. 7,488,719). A perlecan fragment consisting of residue 3464-3707 of the human sequence has been reported to occur in body fluids of multiple sclerosis patients (U.S. Pat. No. 7,510,843). DV has also been reported to enhance binding of collagen to α2 β1 integrin (Bix et al., Blood 109.9 (2007): 3745-48).

BRIEF SUMMARY OF THE INVENTION

The invention provides methods of treating or effecting prophylaxis of an amyloidogenic disease, comprising administering to a patient having or at risk of the disease an effective regime of an agent comprising perlecan domain V (SEQ ID NO:1) or a fragment thereof, or a peptide having at least 85% sequence identity to SEQ ID NO:1 over a comparison window of at least 10 amino acids, wherein the fragment or peptide binds α2β1 integrin. In some methods, the disease is a disease characterized by deposits of Aβ peptide. In some methods, the disease is characterized by deposits of Aβ peptide in the brain of a patient. In some methods, the disease is characterized by deposits of Aβ peptide in the periphery of the patient. In some methods, the disease is Alzheimer's disease, Down's syndrome or mild cognitive impairment. In some methods, the disease is type II diabetes, Parkinson's disease, prion infection, hereditary or systemic amyloidosis. In some methods, the fragment of perlecan domain V comprises or consists of an LG3 domain. In some methods, the fragment of perlecan domain V consists of 5-50 contiguous residues of SEQ ID NO:1. In some methods, the fragment has 5-20 contiguous residues within the LG3 domain of SEQ ID NO:1. In some methods, the agent further comprises a carrier linked to the perlecan domain V, fragment or peptide to facilitate passage across the blood brain barrier, such as a tat peptide.

Some methods further comprise administering an effective regime of an antibody to αv or β1 integrin. In some methods, the antibody inhibits adhesion of αv integrin-expressing cells to vitronectin, fibronectin or osteopontin. In some methods, the inhibitor inhibits adhesion of β1 integrin-expressing cells to fibronectin. In some methods, the antibody is a monoclonal antibody. In some methods, the antibody is or recognizes the same epitope as an antibody selected from among 1965, Lia1/2, Gi9, 1950Z, VNR147, and 1980. In some methods, the antibody competes for binding to αvβ1 with an antibody selected from among 1965, Lia1/2, Gi9, 1950Z, VNR147, and 1980. In some methods, the antibody is a human antibody. In some methods, the antibody is a humanized antibody.

The invention further provides a method of inhibiting Aβ-mediated toxicity, comprising contacting Aβ and cells with perlecan domain V (SEQ ID NO:1) or a fragment thereof, or a peptide having at least 85% sequence identity to SEQ ID NO:1 over a comparison window of at least 10 amino acids, wherein the fragment or variant binds α2β1 integrin wherein the perlecan domain V, fragment or peptide inhibits Aβ-mediated toxicity of the cells. In some methods, the contacting occurs in vitro. In some methods, the contacting occurs in a subject. In some methods, the subject is human. In some methods, the subject is a transgenic animal model of Alzheimer's disease.

The invention further provides a method of screening for an agent comprising contacting the agent with perlecan or a fragment thereof, such as DV or LG3, that binds α2β1 and α2β1 integrin and determining whether the agent modulates binding of perlecan of the fragment to α2β1 integrin. Some such methods also comprise determining whether the agent inhibits Aβ-mediated toxicity of cells. In some such methods, the cells are neuronal cells. Some methods further comprise determining whether the agent reduces Aβ-mediated inhibition of long term potentiation. Some methods further comprise determining whether the agent inhibits a sign or symptom of disease in an animal model of Alzheimer's disease.

The invention further provides for use of an agent comprising perlecan domain V (SEQ ID NO:1) or a fragment thereof, or a peptide having at least 85% sequence identity to SEQ ID NO:1 over a comparison window of at least 10 amino acids, wherein the fragment or peptide binds α2β1 integrin in the manufacture of a medicament for treating or effecting prophylaxis of an amyloidogenic disease.

The invention further provides a method of treating or effecting prophylaxis of an amyloidogenic disease, comprising administering to a patient having or at risk of the disease an effective regime of an agent comprising perlecan domain V (SEQ ID NO:1) or a fragment thereof, or a peptide having at least 85% sequence identity to SEQ ID NO:1 over a comparison window of at least 10 amino acids, wherein the fragment or peptide inhibits Aβ-mediated deposition or toxicity.

The invention further provides a method of treating or effecting prophylaxis of an amyloidogenic disease, comprising administering to a patient having or at risk of the disease an effective regime of an agent comprising perlecan LG3 or a fragment thereof.

DEFINITIONS

Agents of the invention are typically substantially purified from contaminants arising in their production. This means that an agent is typically at least about 50% w/w (weight/weight) purity, as well as being substantially free from interfering proteins and contaminants. Sometimes the agents are at least about 60%, 70%, 80%, 90%, or 95% w/w purity. Using conventional protein purification techniques, homogenous peptides of at least 99% w/w can also be obtained.

Specific binding between two entities means an affinity of at least $10^6$, $10^7$, $10^8$, $10^9$, or $10^{10}$ $M^{-1}$. Specific binding is detectably higher in magnitude and distinguishable from nonspecific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an entity binds one and only one target. Thus, an entity can a show specific binding of different strengths to several different targets and only non-specific binding to other targets.

The term "antibody" or "immunoglobulin" includes intact antibodies and binding fragments thereof. Typically, fragments compete with the intact antibody from which they were derived for specific binding to the target including separate heavy chains, light chains Fab, Fab', F(ab')$_2$, F(ab)c, and Fv. Fragments can be produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

APP[695], APP[751], and APP[770] refer, respectively, to the 695, 751, and 770 amino acid residue long polypeptides encoded by the human APP gene. See Kang et al., Nature, 325:733-36 (1987); Ponte et al., Nature, 331:525-27 (1988); and Kitaguchi et al., Nature, 331:530-32 (1988). Terms such as Aβ39, Aβ40, Aβ41, Aβ42, and Aβ43 refer to an Aβ peptide containing amino acid residues 1-39, 1-40, 1-41, 1-42, and 1-43. Aβ42 has the sequence (SEQ ID NO:2): $H_2N$-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-OH. Aβ41, Aβ40, and Aβ39 differ from Aβ42 (SEQ ID NO:2) by the omission of Ala, Ala-Ile, and Ala-Ile-Val, respectively, from the C-terminal end. Aβ43 differs from Aβ42 (SEQ ID NO:1) by the presence of a threonine residue at the C-terminus.

"Amylin" refers to the human protein of Swiss Prot accession number P10997 or allelic and species variants thereof.

The term "amyloid peptide or protein" refers peptides and proteins that form amyloid-like deposits, including amylin and Aβ. Amyloid deposits comprise a peptide aggregated to an insoluble mass. The nature of the peptide varies in different diseases but in most cases, the aggregate has a β-pleated sheet structure and stains with Congo Red dye, although pre-amyloid deposits may not so stain.

A peptide means a polymer containing at least two amino acids linked by a peptide bond. Peptides can include any number of amino acids.

Amyloidogenic diseases are diseases characterized by amyloid deposits. Amyloidogenic diseases include Alzheimer's disease (AD), both late and early onset. In both late and early AD, the amyloid deposits comprise a peptide termed Aβ, which accumulates in the brain of affected individuals.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996). Antibodies that recognize the same or overlapping epitopes can be identified in a simple immunoassay showing the ability of one antibody to block the binding of another antibody to a target antigen.

The term "patient" includes human and other mammalian subjects that receive either prophylactic or therapeutic treatment.

Unless otherwise apparent from the context, reference to fibronectin includes superfibronectin.

Competition between antibodies is determined by an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay. (see Harlow and Lane, "Antibodies, A Laboratory Manual," Cold Spring Harbor Press (1988)). Typically, such assays involve the use of purified antigen bound to a solid surface or cells bearing either an unlabelled test immunoglobulin or a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%. Analogous methods can be used in determining competition between other entities, such as between an agent and DV or LG3 for binding to α2 integrin.

Unnatural amino acids are amino acids other than the twenty naturally occurring amino acids that are the building blocks for all proteins, but are nonetheless capable of being biologically or chemically engineered such that they are incorporated into proteins. Unnatural amino acids include D-amino acids, β amino acids, and various other "designer" amino acids (e.g., β-methyl amino acids, Cα-methyl amino acids, and Nα-methyl amino acids. Synthetic amino acids include ornithine for lysine, and norleucine for leucine or isoleucine. Hundreds of different amino acid analogs are commercially available from e.g., PepTech Corp., MA. In general, unnatural amino acids have the same basic chemical structure as a naturally occurring amino acid, i.e., a carbon that is bound to a hydrogen, a carboxyl group, an amino group, and an R group. Methods of making and introducing a non-naturally-occurring amino acid into a protein are known. See, e.g., U.S. Pat. Nos. 7,083,970; and 7,524,647.

Modifications of peptides can include N terminus modification, C terminus modification, peptide bond modification, including $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference.

Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of matched and mismatched positions not counting gaps in the window of comparison (i.e., the window size), and multiplying the result by 100 to yield the percentage of sequence identity.

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Compositions or methods "comprising" one or more recited elements may include other elements not specifically recited. For example, a composition that comprises antibody may contain the antibody alone or in combination with other ingredients.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIGS. 2A and B: Aβ binds more robustly to activated α2 integrin expressing cells. FIG. 2A shows micrographs of mouse mammary epithelial (NMuMG3) cells expressing either no alpha2 integrin (vector control), wild-type alpha 2 integrin, or constitutively activated alpha 2 integrin containing the E318A mutation incubated for 72 hours with Aβ and then fixed and stained using the Aβ antibody, 3D6. FIG. 2B shows quantitation of pixels in these micrographs demonstrating a significant increase in Aβ binding to cells expressing wild-type integrin (as compared to vector control cells, **$p<0.05$) that was further enhanced in E318A mutant alpha2 integrin expressing cells (*$p<0.05$).

FIG. 6: Amino acid sequence of human perlecan Domain V (SEQ ID NO:1).

FIG. 8: Alignment of the LG1 (SEQ ID NO:3), LG2 (SEQ ID NO:4), and LG3 (SEQ ID NO:5) domains of human perlecan Domain V.

FIG. 9A shows the results for 18 month old mice.

DETAILED DESCRIPTION OF THE INVENTION

I. General

Figure 5:
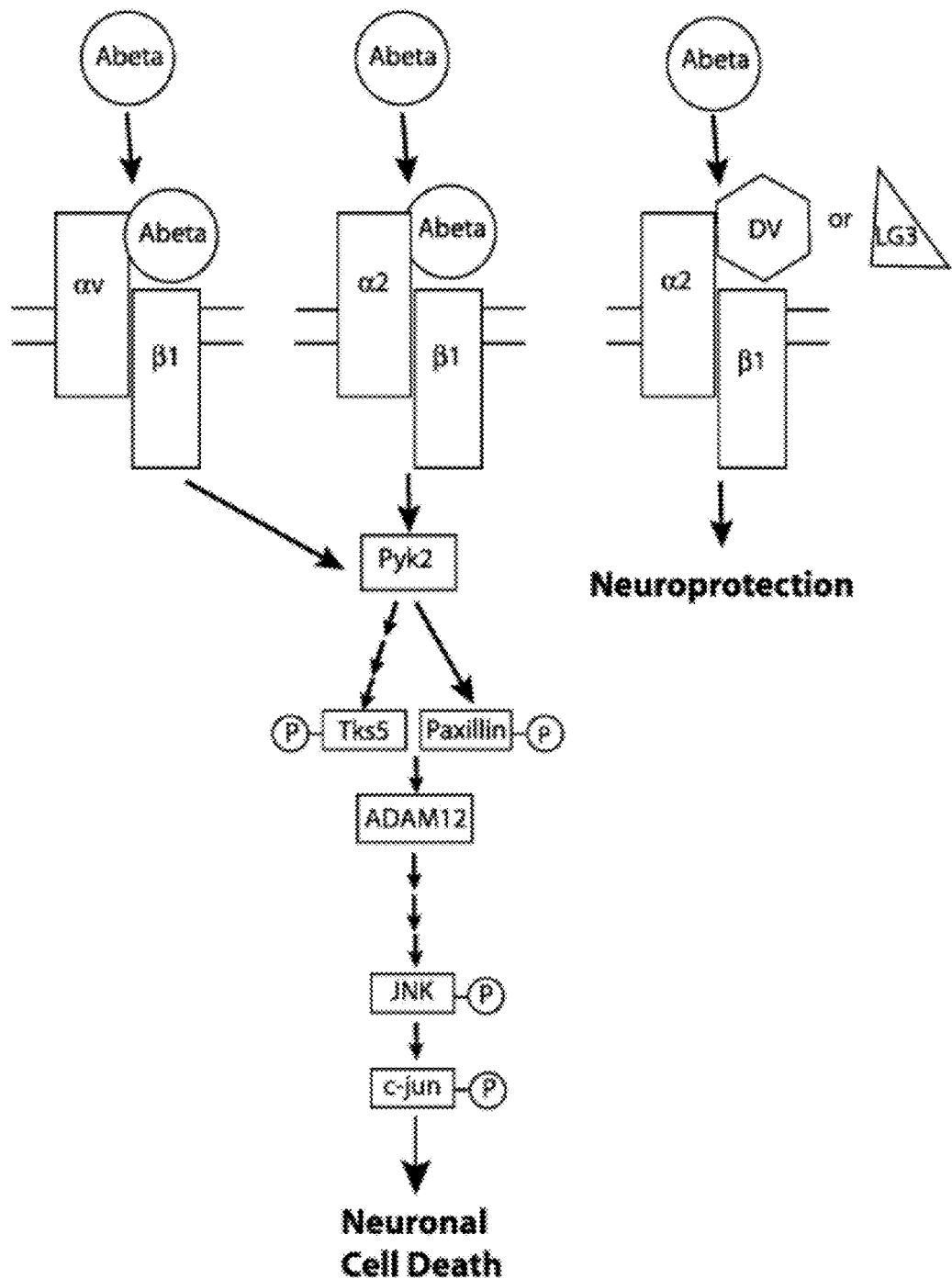
FIG. 5: Model of DV and AP interaction with α2β1 integrin. Aβ beta appears to interact directly with α2 and αv integrin to mediate toxicity in cortical neurons via chronic activation of Pyk2, Tks5, ADAM12 and paxillin leading to JNK activation and neurotoxicity. The presence of Domain V or LG3 can block that interaction, and thus prevent the neurotoxicity.

The invention stems in part from the result that perlecan domain V (DV) reduces deposition and toxicity of Aβ peptide. Although practice of the invention is not depending on an understanding of mechanism, it is believed that DV binds to α2β1 integrin in competition with Aβ thereby reducing binding of Aβ to heterodimeric α2β1 integrin and thereby inhibiting a chain of events by which Aβ mediates toxicity, as shown in FIG. 5. Toxicity and deposition of Aβ can be inhibited using DV and particularly an LG3 subdomain thereof as well as related peptides.

Human recombinant DV is well-tolerated and non-toxic in animal models of disease and specifically homes to pathologic tissue (Bix et al., J. Natl. Cancer Inst. 98.22 (2006): 1634-46). These results can be explained by the fact that DV is a naturally occurring protein fragment readily found in blood and CSF proteomes (Bix & Iozzo, Microsc. Res. Tech. 71.5 (2008): 339-48). Experiments by one of the present inventors in animal models have also shown DV and LG3 can cross the blood brain barrier.

The present results showing a role of DV and LG3 in protecting against Aβ deposition and toxicity provide evidence supporting a therapeutic role for DV, LG3 and related molecules in treatment of amyloidogenic diseases, particularly Alzheimer's disease.

II. Perlecan

The amino acid sequence of human perlecan protein has been assigned Swiss-Prot accession number P98160. The amino acid sequences of residues 3663 to 4391 is reproduced in FIG. 6 (SEQ ID NO:1). Several naturally occurring variants are listed for P98160 in the Swiss-Prot database including an S→N amino acid change at position 4331 (dbSNP rs3736360) occurring within the sequence presented in FIG. 6. The sequence presented in FIG. 6 corresponds to a region of perlecan known as Domain V (DV) (728 amino acids). DV is subdivided into the following regions: residues 3663-3843 (181 amino acids) Laminin G-like domain 1 (LG1); residues 3844-3881 (38 amino acids) EGF-like domain 1; residues 3884-3922 (39 residues) EGF-like domain 2, residues 3928-4103 (176 amino acids), Laminin G-like domain 2 (LG2); residues 4104-4141 (38 amino acids) EGF-like domain 3; residues 4143-4176 (34 amino acids) EGF-like domain 4; residues 4201-4389 (189 amino acids) Laminin G-like domain 3 (LG3). There is a natural BMP-1 cleavage site between residues 4196 and 4197, which generates a peptide of residues 4197-4391 including an LG3 domain. (These delineations between domains are based on the annotations in the Swiss-Prot database for P98160.) Several species variants of the human sequences are known. For example, mouse, *Drosophila* and chicken perlecan are assigned Swiss Prot accession numbers Q05793, Q8MPN3 and Q6 KD71-Chik, respectively; *Macaca mulatta* (rhesus monkey), *Equus caballus* (horse), *Bos taurus* (cow), and *Danio rerio* (zebrafish) perlecan sequences have also been identified.

The invention provides agents comprising or consisting of fragments of perlecan containing a contiguous segment of residues from within DV and preferably from within the laminin-G-like domain 3 region of DV (LG3). Some such agents contain a segment of at least 5, 6, 7, 8, 9, 10, 11, 12, 13, 14, 15, 20, 50, 100, 150, 200, 300, 400, 500, 600, 700 or 728 contiguous residues of SEQ ID NO:1 within DV and/or, in the case of contiguous fragments or segments of 189 amino acids or fewer, within LG3. Some agents contain no more than 700, 600, 500, 400, 300, 200, 100, 50, or 20 contiguous residues of SEQ ID NO:1. For example, some agents have 5-728, 5-500, 5-189, 5-100 or 5-50 contiguous amino acids from SEQ ID NO:1 preferably wholly or partly within LG3. Some agents have 10-728, 10-500, 10-189, 10-100 or 10-50 contiguous amino acids from SEQ ID NO:1, preferably wholly or partly within LG3. Some agents have 20-728, 20-500, 20-189, 20-100 or 20-50 contiguous amino acids from SEQ ID NO:1, preferably wholly or partly within LG3. Some agents have a contiguous segment of residues from SEQ ID NO:1 comprising or consisting of perlecan DV or LG3.

Some exemplary agents include agents comprising or consisting of perlecan peptides defined by any of the following amino acid coordinates in FIG. 2: 4188-4389, 4188-4390, 4188-4391, 4189-4389, 4189-4390, 4189-4391, 4190-4389, 4190-4390, 4190-4391, 4191-4389, 4191-4390, 4191-4391, 4192-4389, 4192-4390, 4192-4391, 4193-4389, 4193-4390, 4193-4391, 4194-4389, 4194-4390, 4194-391, 4195-4389, 4195-4390, 4195-4391, 4196-4389, 4196-4396, 4196-4391, 4197-4389, 4197-4390, 4197-4391, 4198-4389, 4198-4390, 4198-4391, 4199-4389, 4199-4390, 4199-4391, 4200-4389, 4200-4390, 4200-4391, 4201-4389, 4201-4390, 4201-4391, 4202-4389, 4202-4390, 4202-4391. Reference to the peptide 4197-4389, for example, means the peptide beginning at residue 4197 and ending at residue 4389 and including all residues between in FIG. 6. An agent comprising such a peptide may include additional contiguous flanking residues from SEQ ID NO:1. Other peptides are similarly defined. The amino acids in FIG. 6 are numbered with reference to the full-length perlecan sequence of P98160. Because only the DV region of perlecan is shown, the sequence begins at residue 3663. The invention also provide peptides that differ from any of the peptides mentioned above by up to 5, 10, 15, 20, 25 or 50 deletions, additions or substitutions of amino acids. Such deletions, additions or substitutions can be internal or at the C- or N-terminus. Substitutions can be conservative or nonconservative. Additions can include additional contiguous residues from SEQ ID NO:1. Some agents comprise or consist of fragments of any of the above peptides. Some such agents contain a segment of at least 5, 6, 7, 8, 9, 10, 11, 12, 13, 14, 15, 20, 50, 100, 150 amino acids within a specified peptide. Some such agents contain no more than 150, 100, 50, or 20 contiguous residues within a specified peptide. For example, some agents have 5-189, 5-100 or 5-50 contiguous amino acids within a specified peptide. Some agents have 10-100 or 10-50 contiguous amino acids from a specified peptide. Some agents have 20-100 or 20-50 contiguous amino acids from a specified peptide.

Some agents comprise or consist of peptides having amino acid sequences that are variants of SEQ ID NO:1 and or/any other peptide listed above. Such agents can be peptides, typically having at least 85, 90, 95 or 99% sequence identity with SEQ ID NO:1 (or other peptide listed above) over a comparison window of at 10, 25, 50, 100, 200, 300, 400, 500, 600, 700 or 728 amino acids present in both sequences being compared (not including gaps or residues aligned with gaps). The comparison window is preferably within DV and/or LG3. Such peptides preferably have a total length of no more than 800, 700, 600, 500, 400, 300, 200, 100, 50, 20 or 10 amino acids. Some agents have 20-728, 20-500, 20-189, 20-100 or 20-50 amino acids in total. Variants can be species, allelic or induced variants of SEQ ID NO:1. Induced variants can include nonnatural or natural amino acids at positions differing from SEQ ID NO:1. Amino acid substitutions can be conservative or non-conservative.

Figure 8:
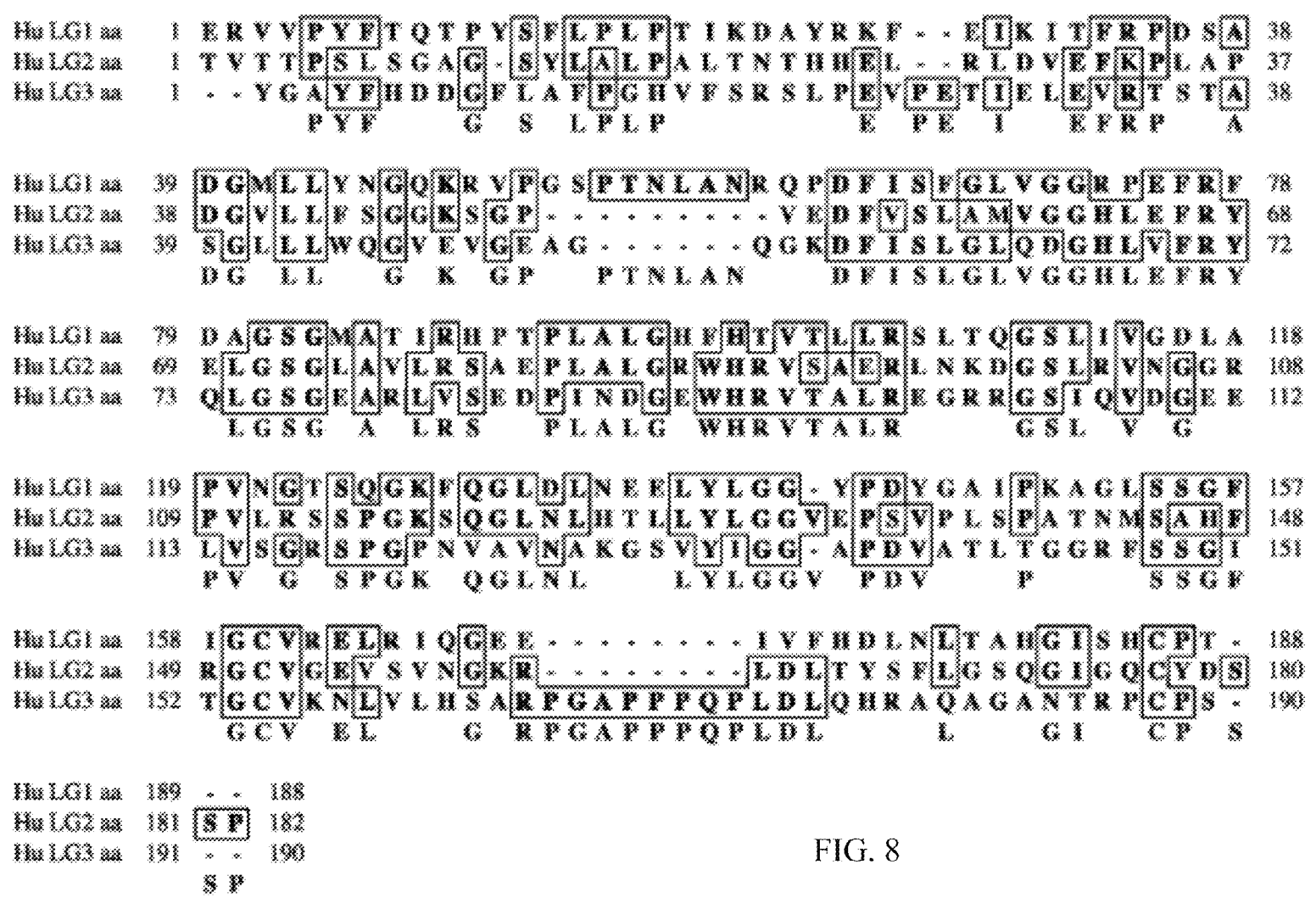

Sequence variants likely to have conserved structure and/or function can be identified by conventional methods. For example, PFam and other domain identification tools can be used to identify amino acids required for the proper folding of protein domains, such as the Laminin G-like (LG) domain or the EGF-like domain. Conserved or conservatively substituted hydrophobic residues found in protein domains that have the same structure but differ in function are often involved in determining secondary and tertiary structure. Multi-sequence alignment tools can be used to identify conserved amino acids in protein domains having related function. Amino acid residues conserved in functionally related domains but not identified as critical for the proper folding of the domain are more likely to relate to the function of the protein domain. Structural prediction tools such as CABS, ESyPred3D, HHpred, ROBETTA, and WHAT IF can be used to model the structure of protein domains, allowing the identification of amino acids located at the surface of a protein domain. Conserved amino acids located at the surface of a protein domain are often involved in protein-protein interactions. In general, variation of amino acids at positions that are neither structurally nor functionally conserved typically results in functional variants; variation of amino acids at positions that are structurally and/or functionally conserved is more constrained, but is sometimes still permissible (e.g., conservative substitutions, and certain non-conservative substitutions may be permissible). The LG3 domain of perlecan DV is a member of the Lamanin_G_1 family (PFam designation PF00054) and contains two DGE sequences forming a binding motif for α2β1 integrin. Perlecan peptides including the two DGE sequences, optionally with some or all intervening amino acids, and with or without additional flanking perlecan sequences are provided, as are agents, comprising or consisting of such peptides. As shown in FIG. 8, the LG1, LG2, and LG3 sequences of human DV can be aligned to highlight structurally conserved amino acid residues. The sequences of DV from different organisms (e.g., human, mouse, rhesus monkey, horse, cow, chicken, and/or zebrafish) can be aligned to reveal structurally and functionally conserved residues. The mouse DV domain, for example, performs similarly to the human in inhibiting Aβ-mediated toxicity. In addition, the LG3 domain can be structurally modeled, e.g., using the structure of pentraxin (see Beckmann et al. (1998), J. Mol. Biol. 275:725-730). The EGF-like domains of perlecan DV are members of the PFam EGF Clan CL0001 and can be structurally modeled based on known EGF-like domain structures. See Hohenester & Engel (2002), Matrix Biol. 21:115-128. Accordingly, using conventional sequence analysis tools and screening methods disclosed in the present application, DV and particularly LG3 sequence variants having conserved structure and function can be identified and tested for function.

Any of the peptides can be natural peptides or can be subject of modifications at the C or N-terminus or side chains.

Some agents include only a peptide segment of SEQ ID NO:1 or a peptide having a high degree of sequence identity (e.g., at least 85, 90, 95 or 99% with SEQ ID NO:1) over the length of the peptide. Other agents include an auxiliary molecule that can be a peptide or non-peptide. Such auxiliary molecules can serve as tags for purposes of identification or to improve pharmokinetics or to improve passage across the blood brain barrier. Examples of peptides that facilitate passage across the blood brain barrier include tat derived from HIV (Vives et al., 1997, J. Biol. Chem. 272:16010; Nagahara et al., 1998, Nat. Med. 4:1449) (e.g., YGRKKRRQRRR), antennapedia from *Drosophila* (Dcrossi et al., 1994, J. Biol. Chem. 261:10444), VP22 from herpes simplex virus (Elliot and D'Hare, 1997, Cell 88:223-233), complementarity-determining regions (CDR) 2 and 3 of anti-DNA antibodies (Avrameas et al., 1998, Proc. Natl. Acad. Sci. U.S.A., 95:5601-5606), 70 kDa heat shock protein (Fujihara, 1999, EMBO J. 18:411-419) and transportan (Pooga et al., 1998, FASEB J. 12:67-77).

Some agents lack a peptide segment including residues 3464-3707 of SEQ ID NO:1. Some agents lack any subsegment of 5, 10, 20 or 50 contiguous residues between residues 3464 and 3707 of SEQ ID NO:1. Some agents lack any contiguous segment of at least 5, 10, 20 or 50 residues of SEQ ID NO:1 outside DV. Some agents lack any contiguous segment of at least 5, 10, 20 or 50 residues of SEQ ID NO:1 outside LG3.

Agents of the invention preferably specifically bind to α2 integrin usually when α2 integrin is complexed with β1 integrin. Agents of the invention preferably compete with DV and/or LG3 for binding to α2 integrin, again usually tested when complexed with β1 integrin. Agents of the invention also preferably inhibit Aβ-mediated deposition and/or toxicity to neuronal cells as indicated by any of the assays described in the present examples or in US 20090220505. For example, agents can be tested for inhibition of Aβ-mediated deposition on and/or toxicity to human cortical cells. Agents can also be screened for suppression of Aβ-mediated inhibition of long term potentiation in vitro or in vivo as described by US20080193444. Such effects of agents can optionally be compared with control assays in which the agent is absent to demonstrate the agent inhibits Aβ-mediated deposition and/or toxicity and/or long term potentiation.

III. Integrins

Integrins are a superfamily of cell surface adhesion heterodimeric transmembrane receptors, which control the attachment of cells both to the extracellular matrix and to other cells. Adhesion provides anchorages and signals for growth, migration, and differentiation. Integrins are formed by the association of one of about fifteen known α chains with one of about eight known β chains. All human cells except erythrocytes express one or more integrins.

Integrin subunits α2, αv, and β1 are all well known. Exemplary human sequences are retrievable from GenBank accession numbers AF062039, M14648, and X07979, respectively. Various allelic and species variants are described in the Swiss-Prot database. Unless otherwise indicated, reference to α2, αv, and β1 includes these exemplary sequences, allelic variants thereof, species variants and induced variants having at least 85, 90, 95 or 99% sequence identity therewith. Integrins containing αv and one of the β subunits β1, β3, β5, β6 or β8 recognize ligands bearing an RGD motif, but the binding specificity varies depending on which β subunit is present. αvβ1 is known to recognize vitronectin (GenBank accession number X03168), fibronectin (GenBank accession number M26179) and osteopontin (GenBank accession number J04765). Fibronectin is a large multidomain glycoprotein found in connective tissue, on cell surfaces, and in plasma and other body fluids. Fibronectin acts with a variety of macromolecules, including components of the cytoskeleton and the extracellular matrix, circulating components involved in the blood clotting response, fibrinolytic, acute phase and complement systems, and with cell-surface receptors on a variety of cells including fibroblasts, neurons, phagocytes, and bacteria.

Integrins containing α2 and β1 subunits are known as VLA-2 (very late activation antigen 2), GPIa-IIa (glycoprotein Ia-IIa on platelets), and ECMRII (extracellular matrix receptor II). The α2β1 integrins bind collagen-I to VI, laminin and possibly fibronectin. The receptor is expressed on B and T lymphocytes, platelets, fibroblasts, endothelial cells, and melanoma cells, and specifically recognizes collagen and laminins as ligands. Laminins are large, multi domain proteins with a common structural organization. Laminin molecules have alpha, beta, and gamma chain subunits joined together through a coiled coil domain. At least five alpha chains, two beta chains, and three gamma chains are known, and at least twelve laminins having different combinations of these chains have been reported (WO 00/66730). Laminin is found in extracellular matrices including plaques in Alzheimer's disease (Murtomaki, et al., J. Neuro. Res., 32:261-73 (1992); Bronfman, et al., Amyloid: Int. J. Exp. Clin. Invest., 5:16-23 (1998); and Castillo, et al., J. Neuro. Res., 62:451-62 (2000)). Collagen is the most abundant protein in mammals and is the main fibrous component of skin, bone, tendon, cartilage, and teeth. There are more than 23 known collagen genes (Adams et al., Am. J. Respir. Cell. Molec. Biol., 1:161-168 (1989)).

IV. Antibodies to Integrins

Agents including segments from SEQ ID NO:1 or variants of such segments can be administered in combination with antibodies to integrins, such as αv or β1 integrins. Preferably the antibodies bind to the exemplified human sequences provided above. Some antibodies bind αv or β1 as a free subunit or as components of a heterodimer. Other antibodies bind to αvβ1 heterodimer without binding to either subunit in free form or as a component of a different heterodimer.

Binding can be assessed either with isolated integrin subunits or fragments thereof, optionally immobilized to a solid phase, or with integrin subunits expressed on the surface of cells. Often, binding is analyzed using cells expressing a heterodimeric integrin. For example, if an agent specifically binds to cells expressing α2β1 as the only integrin, then it can be concluded that the agent specifically binds to α2 or β1 or to α2β1 without specifically binding to either subunit alone. These possibilities can be distinguished by testing binding of the same agent to cells bearing a different heterodimeric integrin. For example, if the same agent specifically binds to cells bearing αvβ1 as the only integrin present, then it is likely that the agent is binding to the β1 subunit. A variety of antibodies to integrin and integrin subunits are commercially available, some of which are described in the Examples.

Monoclonal or polyclonal antibodies can be used in the methods of the invention. Preferred antibodies block interaction of αv or β1 integrin subunits with one or more of their natural ligands, including fibronectin, osteopontin and/or vitronectin. For example, the 14D9.F8 antibody described by WO 99/37683 blocks binding of αv to fibronectin. The capacity of an antibody or other agent to block can be recognized by a simple assay in which cells expressing an integrin are tested for adhesion to a plate coated with ligand in the presence or absence of antibody (or other agent). A reduction of at least about 30%, 40%, 50%, 60%, 70%, 80%, 90%, or 100% of the amount of cells binding to the plate identifies a blocking antibody (or other agent) when the antibody is present in molar excess relative to the integrin. Further analyses of the blocking capacity of the agent to other combinations of integrin subunits can pinpoint which subunit of a heterodimeric integrin is being blocked. Binding specificity of an antibody or other agent can also be determined by a competition assay in which a test antibody competes with a reference antibody known to have the desired epitope specificity for binding to an integrin subunit or cells bearing the same. If the test and reference antibodies compete, then they bind to the same epitope or epitopes sufficiently proximal that binding of one antibody interferes with binding of the other.

Antibodies are typically first evaluated for specific binding to an integrin subunit αv or β1. Suitable agents typically bind with specific affinities of at least $10^7$, $10^8$, $10^9$ or $10^{10}$ M$^{-1}$.

Thereafter, antibodies are optionally evaluated for a particular epitope specificity. This can be determined by a competition assay with a reference agent, by a functional plate blocking assay as described above, or by an epitope mapping experiment in which an antibody or other agent is evaluated by Western blotting or ELISA for its capacity to bind a series of deletion mutants of an antigen. The smallest fragment to show specific binding to the antibody or other agent defines the epitope of the antibody or other agent. Alternatively, or additionally, antibodies can be evaluated for the capacity to inhibit formation of extracellular meshworks of amyloid peptides. Suitable antibodies typically reduce toxicity resulting from treatment with amyloid peptides, such as Aβ, relative to a control by at least about 10%, 20%, 30%, 40%, 50%, 60%, 70%, 80%, 90%, or 100% or more.

The antibodies used in the present methods can be intact antibodies or binding fragments, such as Fabs, Fvs, single-chain antibodies in which VH and VL are linked through a spacer, nanobodies derived from camelids or the like (Ablynx) or dAbs (VH or VL) (Domantis). Antibodies can be monoclonal or polyclonal. Some antibodies are non-human, particularly, mouse antibodies. Some examples of commercially available mouse antibodies are shown in Table 1. 20A9 and 18C7 (CA1Biochem and U.S. Pat. No. 7,829,087) are other antibodies to human αv that can be used.

TABLE 1

| Antibody | Supplier | Antigen | Ligand Blocked |
|---|---|---|---|
| VNR147 | Gibco or Chemicon | Human αv integrin | fibrinogen and vitronectin |
| MAB1980 | Chemicon | Human αv integrin | vitronectin |
| IM1603 | Immunotech | Human αv integrin | vitronectin |
| Lia1/2 | Immunotech | Human β1 integrin | fibronectin |
| MAB1965 | Chemicon | Human β1 integrin | collagen and fibronectin |
| AIIB2 | Caroline Damsky, UCSF | Human β1 integrin | fibronectin |
| 17E6 | Calbiochem | Human αv integrin | fibronectin and vitronectrin |

Chimeric and humanized antibodies may have the same or similar binding specificity and affinity as a mouse or other nonhuman antibody that provides the starting material for construction of a chimeric or humanized antibody (e.g., any of the mouse antibodies described above or in the examples). Some chimeric or humanized antibodies have affinities within a factor of 2-fold, 5-fold or 10-fold that of a mouse. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1, IgG2, IgG3, or IgG4. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions, preferably as defined by Kabat, entirely or substantially from a nonhuman antibody such as a mouse-antibody, (referred to as the donor immunoglobulin). See Queen et al., Proc. Nat. Acad. Sci. U.S.A., 86:10029-33 (1989) and WO 90/07861, U.S. Pat. No. 5,693,762, U.S. Pat. No. 5,693,761, U.S. Pat. No. 5,585,089, U.S. Pat. No. 5,530,101, and Winter, U.S. Pat. No. 5,225,539 (each of which are incorporated herein by reference in their entirety for all purposes). The constant region, if present, is also substantially or entirely from a human immunoglobulin. By way of example, a humanized antibody can include Kabat CDRs entirely from a donor antibody (i.e., three heavy and three light chain Kabat CDRs), and heavy and light chain variable region frameworks substantially from (e.g., at least 85% sequence identity to) a human antibody sequence, which can be, for example, a mature, genomic or consensus human antibody sequence.

Human antibodies to αv or β1 can also be used. Human antibodies can be made by a variety of methods, including the trimoma approach of Oestberg et al., Hybridoma, 2:361-67 (1983); Oestberg, U.S. Pat. No. 4,634,664; and Engleman et al., U.S. Pat. No. 4,634,666; non-human transgenic mammals having transgenes encoding at least a segment of the human immunoglobulin locus (e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, Nature 148, 1547 53 (1994), Fishwild et al., Nature Biotechnology, 14, 845 51 (1996), Kucherlapati, WO 91/10741 (1991)); or phage display (see, e.g., Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743, U.S. Pat. No. 5,565,332, U.S. Pat. No. 5,969,108, U.S. Pat. No. 6,172,197; WO 92/20791).

The heavy and light chain variable regions of chimeric, humanized, or human antibodies can be linked to at least a portion of a human constant region. The choice of constant region depends, in part, on whether antibody dependent complement and/or cellular mediated toxicity is desired. For example, isotypes IgG1 and IgG3 have complement activity and isotypes IgG2 and IgG4 do not. Choice of isotype can also affect passage of the antibody into the brain. Light chain constant regions can be lambda or kappa.

V. Animal Screens

Agents including segments from SEQ ID NO:1 or variants of such segments, optionally in combination with antibodies to αv or β1 integrin can be tested for prophylactic and therapeutic efficacy in transgenic animals predisposed to an amyloidogenic disease. Such animals include, for example, mice bearing a 717 mutation of APP described by Games et al., supra, and mice bearing a 670/671 Swedish mutation of APP such as described by McConlogue et al., U.S. Pat. No. 5,612,486; Hsiao et al., Science, 274:99 (1996); Sturchler-Plerrat et al., Proc. Natl. Acad. Sci. U.S.A., 94:13287-92 (1997); and Borchelt et al., Neuron, 19:939-45 (1997). Activity of agents can be assessed from total content of Aβ in the brain or a region thereof, histochemical detection of deposits in brain sections, neuronal cells pathology, such as neuritic dystrophy or LTP, or markers thereof, such as synaptophysin, cells mediating inflammation, such as activated astrocytes or microglial cells, or by cognitive testing. Activity can be shown by a reduction in Aβ deposits, pathology, reduced inflammation, reduced neuronal toxicity, increased synaptophysin or LTP, or reduced impairment of cognitive function in transgenic animals treated with an agent relative transgenic animals administered a placebo or nothing. Agents showing activity in transgenic mice can then be evaluated in human clinical trials. Exemplary formats for conducting human clinical trials in Alzheimer's patients are described in WO 98/24678, which is incorporated herein by reference.

VI. Other Agents and Screening Methods

The invention provides methods of screening to identify agents acting as agonists or mimetics of DV or LG3-mediated protection from amyloid toxicity. Agonists can act by promoting binding of DV or LG3 (or related agents) to α2, optionally in combination with β1. Mimetics can by themselves bind α2, optionally in combination with β1, at the same site or an overlapping site on DV or LG3, such that binding of the mimetic inhibits binding of Aβ or other amyloidogenic peptide to α2β1 integrin.

Agents to be screened can be naturally occurring or synthetic molecules. Agents to be screened can also be obtained from natural sources, such as, e.g., marine microorganisms, algae, plants, and fungi. Alternatively, agents to be screened can be from combinatorial libraries of agents, including peptides or small molecules, or from existing repertories of chemical compounds synthesized in industry, e.g., by the chemical, pharmaceutical, environmental, agricultural, marine, cosmeceutical, drug, and biotechnological industries. Agents can include, e.g., pharmaceuticals, therapeutics, environmental, agricultural, or industrial agents, pollutants, cosmeceuticals, drugs, organic compounds, lipids, glucocorticoids, antibiotics, peptides, proteins, sugars, carbohydrates, and chimeric molecules.

A variety of methods are available for producing peptide libraries (see, e.g., Lam et al., Nature, 354:92, 1991 and WO 92/00091; Geysen et al., J. Immunol. Meth., 102:259 (1987); Houghten et al., Nature, 354:84 (1991); WO 92/09300; and Lebl et al., Int. J. Pept. Prot. Res., 41:201 (1993)). Peptide libraries can also be generated by phage display methods. See, e.g., Devlin, WO 91/18980.

Combinatorial libraries can be produced for many types of compounds that can be synthesized in a step by step fashion (see e.g., Ellman & Bunin, J. Amer. Chem. Soc., 114:10997, 1992 (benzodiazepine template), WO 95/32184 (oxazolone and aminidine template), WO 95/30642 (dihydrobenzopyran template), and WO 95/35278 (pyrrolidine template)). Libraries of compounds are usually synthesized by solid phase chemistry. However, solution phase library synthesis can also be useful. Strategies for combinatorial synthesis are described by Dolle & Nelson, J. Combinatorial Chemistry, 1:235 282 (1999) (incorporated herein by reference in its entirety for all purposes). Synthesis is typically performed in a cyclic fashion with a different monomer or other component being added in each round of synthesis. Some methods are performed by successively fractionating an initial pool. For example, a first round of synthesis is performed on all supports. The supports are then divided into two pools and separate synthesis reactions are performed on each pool. The two pools are then further divided, each into a further two pools and so forth. Other methods employ both splitting and repooling. For example, after an initial round of synthesis, a pool of compounds is split into two for separate syntheses in a second round. Thereafter, aliquots from the separate pools are recombined for a third round of synthesis. Split and pool methods result in a pool of mixed compounds. These methods are particularly amenable for tagging as described in more detail below. The size of libraries generated by such methods can vary from 2 different compounds to $10^6$, or $10^{10}$, or any range there between.

Preparation of encoded libraries is described in a variety of publications including Needels, et al., Proc. Natl. Acad. Sci. U.S.A., 90:10700 (1993); Ni, et al., J. Med. Chem., 39:1601

(1996), WO 95/12608, WO 93/06121, WO 94/08051, WO 95/35503, and WO 95/30642 (each of which is incorporated herein by reference in its entirety for all purposes). Methods for synthesizing encoded libraries typically involve a random combinatorial approach and the chemical and/or enzymatic assembly of monomer units. For example, the method typically includes steps of: (a) apportioning a plurality of solid supports among a plurality of reaction vessels; (b) coupling to the supports in each reaction vessel a first monomer and a first tag using different first monomer and tag combinations in each different reaction vessel; (c) pooling the supports; (d) apportioning the supports among a plurality of reaction vessels; (e) coupling to the first monomer a second monomer and coupling to either the solid support or to the first tag a second tag using different second monomer and second tag combinations in each different reaction vessel; and optionally repeating the coupling and apportioning steps with different tags and different monomers one to twenty or more times. The monomer set can be expanded or contracted from step to step; or the monomer set could be changed completely for the next step (e.g., amino acids in one step, nucleosides in another step, carbohydrates in another step). A monomer unit for peptide synthesis, for example, can include single amino acids or larger peptide units, or both.

Compounds synthesizable by such methods include polypeptides, beta turn mimetics, polysaccharides, phospholipids, hormones, prostaglandins, steroids, aromatic compounds, heterocyclic compounds, benzodiazepines, oligomeric N substituted glycines, and oligocarbamates. Prepared combinatorial libraries are also available from commercial sources (e.g., ChemRx, South San Francisco, Calif.).

Combinatorial libraries and other compounds are initially screened in a binding assay with α2 integrin optionally complexed with beta 1 integrin and DV or LG3 or a peptide fragment of one of these. Compounds that increase or decrease binding of DV, LG3 or peptide fragments of these to α2 integrin can be useful as agonists or mimetics of DV or LG3. Such compounds can be further tested for inhibition of Aβ-induced α2β1 integrin-mediated signaling (e.g., inhibition of c-jun phosphorylation, JNK phosphorylation, paxillin phosphorylation, Tks5 phosphorylation, and/or Pyk2 activation), protection against amyloid toxicity in vitro, and protection against amyloid toxicity in animal models, as described for other compounds.

VII. Nucleic Acids Encoding Therapeutic Agents

Antibody or other peptide reagents can be administered in the form of nucleic acids encoding antibody chains or peptides. Such nucleic acids are typically linked to regulatory elements, such as a promoter and enhancer, that allow expression of the DNA segment in the intended target cells of a patient. Promoter and enhancer elements from light or heavy chain immunoglobulin genes or the cytomegalovirus (CMV) major intermediate early promoter and enhancer are suitable to direct expression. In some methods promoters that cause expression in the brain are used. Promoters such as platelet-derived growth factor (PDGF), prion, or the neural enolase promoter are suitable.

The linked regulatory elements and coding sequences are often cloned into a vector. For administration of double chain antibodies, the two chains can be cloned in the same or separate vectors.

A number of viral vector systems are available including retroviral systems (see, e.g., Lawrie and Tumin, Curr. Opin. Genet. Develop., 2:102 109 (1993)); adenoviral vectors (see, e.g., Bett et al., J. Virol., 67:5911 (1993)); adeno associated virus vectors (see, e.g., Zhou et al., J. Exp. Med., 179:1867 75 (1994)), viral vectors from the pox family including vaccinia virus and the avian pox viruses, viral vectors from the alpha virus genus such as those derived from Sindbis and Semliki Forest Viruses (see, e.g., Dubensky et al., J. Virol., 70:508 19 (1996)), Venezuelan equine encephalitis virus (see U.S. Pat. No. 5,643,576), rhabdoviruses, such as vesicular stomatitis virus (see WO 96/34625), and papillomaviruses (Ohe et al., Human Gene Therapy, 6:325 33 (1995); Woo et al., WO 94/12629; and Xiao & Brandsma, Nucleic Acids. Res., 24:2630 22 (1996)).

DNA can be packaged into liposomes. Suitable lipids and related analogs are described by U.S. Pat. Nos. 5,208,036, 5,264,618, 5,279,833, and 5,283,185. Vectors and DNA encoding an immunogen can also be adsorbed to or associated with particulate carriers, examples of which include polymethyl methacrylate polymers, polylactides, and poly (lactide co glycolides).

Gene therapy vectors or naked DNA can be delivered in vivo by administration to an individual patient, typically by systemic administration (e.g., intravenous, intraperitoneal, nasal, gastric, intradermal, intramuscular, intrathecal, subdermal, or intracranial infusion) or topical application (see, e.g., U.S. Pat. No. 5,399,346). Such vectors can further include facilitating agents such as bupivacine (U.S. Pat. No. 5,593, 970). DNA can also be administered using a gene gun. See Xiao & Brandsma, supra. The DNA is precipitated onto the surface of microscopic metal beads. The microprojectiles are accelerated with a shock wave or expanding helium gas, and penetrate tissues to a depth of several cell layers. For example, the Accel™ Gene Delivery Device manufactured by Agacetus, Inc., Middleton, Wis. is suitable. Alternatively, naked DNA can pass through skin into the blood stream simply by spotting the DNA onto skin with chemical or mechanical irritation (see WO 95/05853).

In a further variation, nucleic acids can be delivered to cells ex vivo, such as cells explanted from an individual patient (e.g., lymphocytes, bone marrow aspirates, tissue biopsy) or universal donor hematopoictic stem cells, followed by reimplantation of the cells into a patient, usually after selection for cells that have incorporated the vector.

VIII. Patients Amenable to Treatment

The present methods are useful for prophylactic or therapeutic treatment of several amyloidogenic diseases and conditions that are characterized by the presence of deposits of amyloid peptides, particularly Aβ peptide. The methods are particularly amenable to treatment of diseases characterized by deposits of Aβ in the brain, such as Alzheimer's disease, Down's syndrome, mild cognitive impairment, cerebral amyloid angiopathy (characterized by deposits in blood vessels in the brain), and some forms of Lewy body disease including Parkinson's disease. Diseases characterized by deposits of Aβ in the periphery, or deposits of other amyloidogenic peptides in either the brain or periphery (e.g., synucleinopathic diseases, such as Parkinson's characterized by deposits of alpha synuclein, type II diabetes, characterized by amylin deposits, Parkinson's disease characterized by alpha-synuclein deposits, Huntington's disease characterized by huntingtin deposits, diseases resulting from prion infection, such as Creutzfeldt-Jakob disease, mad cow disease, sheep scrapie, and mink spongiform encephalopathy. Other amyloidogenic diseases that can be treated include multiple myeloma characterized by deposits of cystatin C, rheumatoid arthritis characterized by deposits of serum amyloid A, atherosclerosis characterized by deposits of apolipoprotein A1, cardiac arrythmias characterized by deposits of Atrial natriuretic factor and hereditary or systemic amyloidoses including those mediated by transthyretin (TTR), immunoglobulin light chain and amyloid A deposition.

Patients amenable to treatment include individuals at risk of disease but not showing symptoms, as well as patients presently showing symptoms. In the case of Alzheimer's disease, virtually any human is at risk of suffering from Alzheimer's disease if he or she lives long enough. The present methods can be used for individuals with or without known genetic risk of disease. Such individuals include those having relatives who have experienced this disease, and those whose risk is determined by analysis of genetic or biochemical markers. Genetic markers of risk toward Alzheimer's disease include mutations in the APP gene, for example mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of AD, hypercholesterolemia, or arteriosclerosis. Individuals presently suffering from Alzheimer's disease can be recognized from characteristic dementia, as well as the presence of the risk factors described above. In addition, a number of diagnostic tests are available for identifying individuals who have AD. These include measurement of cerebrospinal fluid (CSF) tau and Aβ42 levels. Elevated tau and decreased Aβ42 levels signify the presence of AD. Individuals suffering from Alzheimer's disease can also be diagnosed by ADRDA criteria. In asymptomatic patients, treatment can begin at any age (e.g., about 10, about 20, about 30). Usually, however, it is not necessary to begin treatment until a patient reaches about 40, about 50, about 60, about 70, about 80 or about 90. Treatment typically entails multiple dosages over a period of time. In the case of Down's syndrome patients, treatment can begin prenatally by administering therapeutic agents to the mother; or treatment may begin shortly after birth.

IX. Treatment Regimes

In prophylactic applications, pharmaceutical compositions or medicaments are administered to a patient susceptible to, or otherwise at risk of developing an amyloidogenic disease, in a regime (i.e., dose, frequency, route of delivery) sufficient to at last reduce the risk, lessen the severity, or delay the onset of the disease, including biochemical, histological and/or behavioral symptoms of the disease, its complications and intermediate pathological phenotypes presenting during development of the disease.

In therapeutic applications, compositions or medicaments are administered to a patient suspected of, or already suffering from such a disease in a regime (dose, frequency, route) sufficient to reduce, or at least slow deterioration of the symptoms of the disease (biochemical, histological, and/or behavioral), including its complications and intermediate pathological symptoms. An amount adequate to accomplish therapeutic or prophylactic treatment is defined as a therapeutically- or prophylactically effective dose. In therapeutic regimes, the agent is usually administered at intervals until symptoms of the disease disappear or significantly decrease. Optionally administration can be continued to prevent recurrence. In prophylactic regimes, agents are also usually administered at intervals, in some instances for the rest of a patient's life. Treatment can be monitored by assaying levels of administered agent, or by monitoring the response of the patient. The response can be monitored by the Alzheimer's Disease and Related Disorders Association (ADRDA) criteria and imaging of plaques or neuronal pathology in the brain of the patient by MRI or positive emission tomography (PET). [$^{11}$C] (Pittsburgh Compound-B) is a ligand to Aβ useful for PET. Successful treatment is shown by reduction in plaques and/or neuronal pathology or at least inhibition of further increases, and/or increased cognitive function or least inhibition of further deterioration in cognitive function.

Effective doses of the compositions of the present invention, for the treatment of the above-described conditions vary depending upon many different factors, including means of administration, target site, physiological state of the patient, whether the patient is human or an animal, other medications administered, and whether treatment is prophylactic or therapeutic. Usually, the patient is a human; nonhuman mammals, including transgenic mammals, can also be treated. Treatment dosages are typically titrated to optimize safety and efficacy.

Dosages of antibodies, peptides, and small molecules range from about 0.0001 to about 100 mg/kg, and more usually about 0.01 to about 20 mg/kg, of the host body weight. For example, dosages can be about 1 mg/kg body weight or about 20 mg/kg body weight or within the range of about 1 to about 10 mg/kg or 1-5 mg/kg. An exemplary treatment regime entails administration once per day, week, every two weeks or once a month or once every 3 to 6 months.

In methods in which antibodies are administered with DV, LG3 or related peptides, the antibody can be administered at the same or different time than the peptide. Antibody is usually administered on multiple occasions. Intervals between single dosages can be weekly, monthly or yearly. Intervals can also be irregular as indicated by measuring blood levels of antibody to integrins in the patient. In some methods, dosage of antibody is adjusted to achieve a plasma antibody concentration of about 1 to about 1000 μg/ml, and in some methods about 25 to about 300 μg/ml. Alternatively, antibody can be administered as a sustained release formulation, in which case less frequent administration is required. Dosage and frequency vary depending on the half life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until the progression of the disease is reduced or terminated, and preferably until the patient shows partial or complete amelioration of the symptoms of the disease. Thereafter, the patient can be administered a prophylactic regime.

Doses for nucleic acid encoding agents range from about 10 ng to 1 g, about 100 ng to about 100 mg, about 1 μg to about 10 mg, or about 30 to about 300 μg DNA per patient. Doses for infectious viral vectors may vary from about 10 to about 100, or about $10^3$, about $10^4$, about $10^5$, about $10^6$, about $10^7$, about $10^8$, about $10^9$, about $10^{10}$, or more virions per dose.

Agents of the invention can be administered by parenteral, topical, intravenous, oral, subcutaneous, intrathecal, intraarterial, intracranial, intraperitoneal, intranasal, or intramuscular means for prophylactic and/or therapeutic treatment. In some methods, agents are injected directly into a particular tissue where deposits have accumulated, for example, intracranial injection. In some methods, intramuscular injection or intravenous infusion are employed for the administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in the treatment of amyloidogenic disease. In the case of Alzheimer's disease and Down's syndrome, in which amyloid deposits occur in the brain, agents of the invention can also be administered in conjunction with other agents that increase passage of the agents of the invention across the blood brain barrier, such as mannitol, Tween® or DMSO.

Agents of the invention are often administered as compositions comprising an active therapeutic agent and a variety of other pharmaceutically acceptable components. See Remington's Pharmaceutical Science (15th ed., Mack Publishing Company, Easton, Pa., 1980). The particular formulation employed depends on the intended mode of administration and the therapeutic application. The compositions can also include, depending on the formulation desired, pharmaceutically acceptable, non toxic carriers or diluents, which are defined as vehicles commonly used to formulate pharmaceutical compositions for animal or human administration. The diluent is selected so as not to negatively impact the biological activity of the combination. Examples of such diluents include, but are not limited to, distilled water, physiological phosphate-buffered saline, Ringer's solution, dextrose solution, and Hank's solution. In addition, the pharmaceutical composition or formulation may also include other carriers, adjuvants, or nontoxic, nontherapeutic, nonimmunogenic stabilizers, and the like.

Pharmaceutical compositions can also include large, slowly metabolized macromolecules such as proteins, polysaccharides such as chitosan, polylactic acids, polyglycolic acids, copolymers (such as latex functionalized Sepharose™ beads, agarose, cellulose, and the like), polymeric amino acids, amino acid copolymers, and lipid aggregates (such as oil droplets or liposomes).

For parenteral administration, agents of the invention can be administered as injectable dosages of a solution or suspension of the substance in a physiologically-acceptable diluent with a pharmaceutical carrier that can be a sterile liquid such as water, oils, saline, glycerol, or ethanol. Parenteral compositions for human administration are sterile, substantially isotonic, and made under GMP conditions. Additionally, auxiliary substances, such as wetting or emulsifying agents, surfactants, pH buffering substances, and the like, can be present in compositions. Other components of pharmaceutical compositions are those of petroleum, animal, vegetable, or synthetic origin, for example, peanut oil, soybean oil, and mineral oil. In general, glycols, such as propylene glycol or polyethylene glycol, are preferred liquid carriers, particularly for injectable solutions. Antibodies can be administered in the form of a depot injection or implant preparation that can be formulated in such a manner as to permit a sustained release of the active ingredient. An exemplary composition comprises monoclonal antibody at 5 mg/mL, formulated in aqueous buffer containing 50 mM L-histidine (optional), 150 mM NaCl, adjusted to a suitable pH with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or microparticles such as polylactide, polyglycolide, or copolymer for enhanced adjuvant effect, as discussed above (see Langer, Science, 249:1527 33 (1990) and Hanes et al., Advanced Drug Delivery Reviews, 28:97-119 (1997). The agents of this invention can be administered in the form of a depot injection or implant preparation that can be formulated in such a manner as to permit a sustained or pulsatile release of the active ingredient.

Additional formulations suitable for other modes of administration include oral, intranasal, and pulmonary formulations, suppositories, and transdermal applications. Intranasal delivery is particularly useful for delivering peptides to the brain. Peptides can be formulated, for example, in sterile water, as a nasal spray. For suppositories, binders and carriers include, for example, polyalkylene glycols or triglycerides; such suppositories can be formed from mixtures containing the active ingredient in the range of about 0.5% to about 10%, or about 1% to about 2%. Oral formulations can include excipients such as pharmaceutical grades of mannitol, lactose, starch, magnesium stearate, sodium saccharine, cellulose, and magnesium carbonate. These compositions typically take the form of solutions, suspensions, tablets, pills, capsules, sustained release formulations or powders and contain about 10% to about 95% of active ingredient, or about 25% to about 70%.

Topical application can result in transdermal or intradermal delivery. Topical administration can be facilitated by co administration of the agent with cholera toxin or detoxified derivatives or subunits thereof or other similar bacterial toxins (See Glenn et al., Nature, 391:851 (1998)). Coadministration can be achieved by using the components as a mixture or as linked molecules obtained by chemical crosslinking or expression as a fusion protein. Alternatively, transdermal delivery can be achieved using a skin patch or using transfersomes (Paul et al., Eur. J. Immunol., 25:3521 24 (1995); Cevc et al., Biochem. Biophys. Acta, 1368:201 15 (1998)).

EXAMPLES

Example 1

1. Materials and Methods 1.1. Tissue Culture

Human cortical (HCC) and mouse cortical (MCC) cultures from α2 null mice and wild type littermate controls in a C57B16 background (kindly provided by Mary Zutter, Vanderbilt University) were prepared as described in Wright et al. (2007), Neurobiol. Aging 28:226-37. Human fetal cerebral cortical tissue was obtained by Advanced Bioscience Resources (Alameda, Calif.) and complied with federal guidelines for fetal research and with the Uniformed Anatomical Gift Act.

1.2 Aβ Preparation

Aβ(1-40) and (1-42) preparation and characterization was conducted as described previously (Wogulis et al. Neurosci. 25.5 (2005): 1071-80). For some experiments Aβ lots preselected to have an appropriate ratio of aggregated to soluble Aβ to generate the equivalent of two component toxicity when made up as a ddH$_2$0 stock were also used. These were prepared by adding ddH$_2$0 to Aβ powder to make 1 mM solution. The solution was immediately aliquoted and frozen.

1.3. Domain V and LG3 Preparation/Purification

Human Domain V (DV) was cloned into the vector pSecTag2A (Invitrogen) using the following primers: 5' DV Asci pSecTag 2A: 5'-ACC GCG CCC CAT CAA GAT CAC CTT CCG GC-3' (SEQ ID NO:6); 3' DV Xho1 pSEc Tag 2A: 5'-AGC TCG AGC CGA GGG GCA GGG GCG TGT GTT G-3' (SEQ ID NO:7). The DV cDNA was amplified from HUVEC cDNA utilizing a GC-rich PCR system and dNT-Pack (Roche Applied Science, Indianapolis, Ind.) and used the restriction enzymes Xho1, Asc1 (NEB Corp., Ipswich, Mass.). Maxi-preps of DV DNA were transfected into 293FT (ATCC, Manassas, Va.) cells via lipofectamine (Invitrogen). After transfection, the 293 cells were exposed to serum-free media for 48-72 hours followed by collection and DV purification via its C-terminal 6×His tag and Ni-ATA agarose bead (Qiagen, Valencia, Calif.) as per the company's instructions. Eluted fractions that contained DV were combined and dialyzed against 1×PBS and the purity of the resultant DV was confirmed via SDS-PAGE stained with Brilliant Blue G-colloidal and by western blot analysis using commercially available anti-DV antibody (R&D systems, Minneapolis, Minn.) and anti-His antibody (EMD Chemicals, Gibbstown, N.J.). The DV was quantified with Quick Start Bradford Dye Reagent.

The LG3 C-terminal domain of DV was cloned and ligated using the pCEP-PU vector using the following primers: 5'-AGG CAT ACG CAT GGC ATA GCA ATA GCA GAG TC-3' (SEQ ID NO:8)(the final sequence included a NheI linker at the 3' end); and 5'-AGC TCG AGC ATG ATG ATG ATG ATG ATG CGA GG-3' (SEQ ID NO:9)(the final sequence included a XhoI linker at the 3' end). These primers amplify DNA encoding a perlecan peptide of amino acids 4188-4391 of FIG. 6 including an LG3 domain and a BMP-1 cleavage site. LG3 was expressed in 293FT cells and purified via an added C-terminal 6×His tag in an identical fashion to DV. Activity of DV and LG3 was confirmed by HUVEC adhesion assays, performed as previously described (Mongiat et al. (2003), J. Biol. Chem. 278:4238-49) in which DV or LG3 prevented HUVEC adhesion to collagen 1 (BD Biosciences, Franklin Lakes, N.J., USA) or fibronectin (Sigma, St. Louis, Mo., USA).

1.4 Aβ Treatments in Human Cortical Neuronal Cultures

The method of generating Aβ toxicity is described by Wogulis et al., Neurosci. 25.5 (2005): 1071-80). Cells are incubated with indicated concentrations of $ddH_2O$, solubilized Aβ. Doses of Aβ are chosen to generate >60-95% toxicity over the course of 2-3 days, as measured in various assays (Id.). To test antibodies, domain V or LG3 alone, HCC or MCC were pretreated with antibodies or domain V or medium alone for 30 minutes in unsupplemented media followed by ddH20 Aβ solution diluted to indicated concentrations. For cotreatments, domain V or LG3 was added to the cells first, followed by Aβ mixed with integrin antibodies. After two or three days, viability was determined by incubating cells in 10% alamarBlue in basal MMEM for two hours and fluorescent levels measured relative to control and Aβ treated wells (Estus et al. J. Neurosci. 17.20 (1997): 7736-45.). In all cases, cell treatments were performed in triplicate wells. Data is presented as percent inhibition of Aβ toxicity [% INH=((Aβ with antibody/compound values)−(Aβ alone))/(control values-Aβ alone values)*100], and was calculated for each assay in order to compare between assays. For calculations of the 50% effective concentration for inhibition (EC50), the XLfit addin to Excel was used and the sigmoidal dose response model equation [fit=A+((B−A)/(1+ ((C/x)^D)))] for curve fitting. The following list indicates antibodies used in these studies: anti-β1 integrin: MAB1965 (Chemicon); anti-α2 integrin: MAB1950Z (Chemicon), MAB1998 (Chemicon); anti-αV integrin: 17E6 (CD51 Calbiochem). The integrin blocking antibodies were described by the manufacturers to specifically inhibit cellular adhesion through the integrin against which the antibody was directed.

1.5. Aβ Immunofluorescence

Some of the cultures were fixed with 4% paraformaldehyde after the alamar assay and immunostained for the presence of Aβ on the cells as described previously (Wright et al. Neurobiol. Aging 28.2 (2007): 226-37).

1.6 Aβ Binding to Live Cells

Murine NMuMG-3 cells expressing either wild type α2β1 integrin or an activated mutant E318A were maintained in Dulbecco's modified Eagle's medium (Gibco) supplemented with 10% fetal bovine serum, 5 μg/ml insulin, and 850 μg/ml geneticin. Cells were added to chamber slides and allowed to adhere overnight. Nonadherent cells were washed away and medium was exchanged for DMEM containing 25 μM of Amyloid Beta. The slides were incubated for 72 hours at 37° C., 5% $CO_2$. Cells were fixed and immunostained for Aβ using 3D6 as described previously (Wright et al. Neurobiol. Aging 28.2 (2007): 226-37). Slides were imaged on a Nikon Eclipse 80i microscope at 20×. Relative Aβ binding per high power microscopic field was analyzed with Adobe Photoshop CS.

1.7 Western Blotts

Wild-type MCC cultures were treated with DV (300 nM) or medium alone for 30 minutes followed by Aβ 40 (30 μM). After 24 hours the cells were lysed in radioimmuno-precipitation assay (RIPA) buffer, total protein measured, then analyzed by Western blot. Protein lysates of equal total protein were run on 10% SDS-PAGE gels followed by transfer to PDVF membranes. Membranes were blocked for 1 hour in 5% nonfat milk and then incubated overnight in 5% BSA with antibodies to phospho c-jun (serine 63, Cell Signaling, Danvers, Mass., USA). Following a 1-hour incubation in anti-rabbit HRP, the membranes were washed and developed with a chemiluminescent substrate and exposed to film.

Figure 1A:
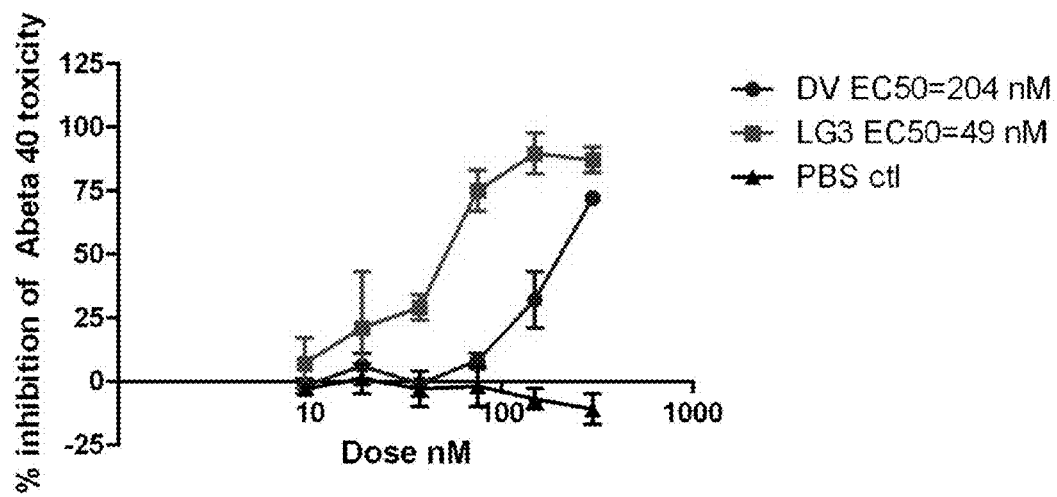
FIGS. 1A and B: Domain V treatment prevents Aβ induced toxicity (A) and deposition (B). A. Error bars in FIG. 1A represent standard deviation of triplicate wells, n>6 experiments conducted.

2. Results 2.1. Domain V and LG3 Potently Inhibit Aβ40 Neurotoxicity in Human Cortical Neurons This example investigates whether domain V or LG3 can block Aβ induced toxicity in the human cortical neurons. Cells were briefly pretreated with domain V or the LG3 fragment of perlecan followed by Aβ40. Domain V robustly inhibited the Aβ-induced neurotoxicity in a dose dependent manner (FIG. 1A). The average EC50 of domain V inhibition of Aβ toxicity was 164 nM (n=5 separate experiments). The molar ratio of the EC50 of inhibition of domain V to the concentration of treated Aβ is about 1:90, showing a substoichiometric relationship to this inhibition. Additionally, LG3 also showed a robust inhibition of Aβ toxicity and was more potent than DV, with an EC50 of 50 nM, also demonstrating a substoichiometric ratio of LG3 to Aβ of about 1:300.

Figure 1B:
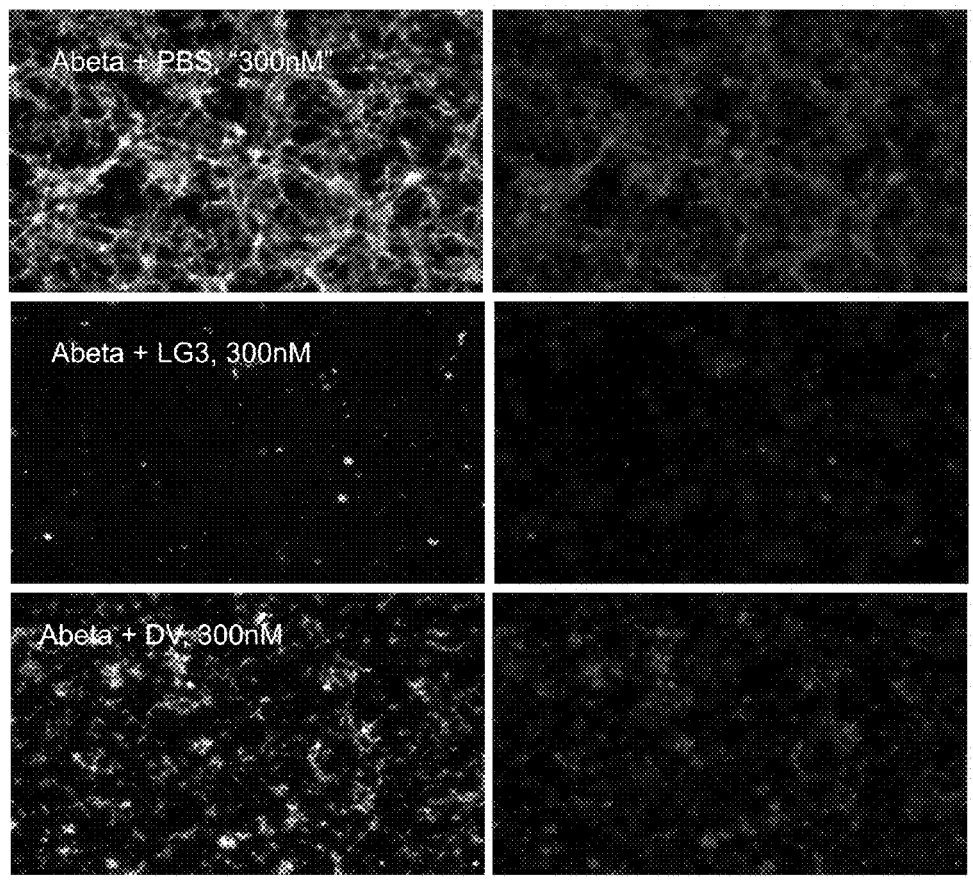
In FIG. 1B, antibody 3D6 staining in Aβ alone conditions showed the formation of meshwork of Aβ depositing on the cells (nuclei stained in blue with DAPI). In the presence of DV, the Aβ deposition is decreased (bottom panel) relative to the control (upper panel) An even greater decrease in Aβ deposition is observed when cells are incubated with LG3 (middle panel).

After assaying the cells for viability, deposition of Aβ onto the cell layer was examined, FIG. 1B. There was also a dose dependent reduction of the Aβ deposited on the cells with both DV and LG3, correlating with the degree of inhibition of toxicity. These results were somewhat variable between experiments, but qualitatively the deposition was decreased in the conditions where toxicity was inhibited.

2.2. Aβ Binds Activated α2 Integrin

Murine mamillary epithelial (NMuMG3) cells that express either no alpha2 integrin, wild-type alpha 2 integrin (12 fold more α2β1 as compared to α2β1 null cells by FACS analysis) or a constitutively activated (i.e. increased affinity for ligand) α2 integrin containing the E318A mutation (at the same expression level as wild-type α2β1 expressing cells by FACS,) were treated with Aβ for 72 h and then fixed and immunostained, FIG. 2A. The wild-type expressing alpha 2 β1 cells bound significantly more Aβ than the alpha 2 β1 null cells, which was further significantly increased in the active alpha 2 integrin expressing cells, as measured by pixel density, FIG. 2B. This finding provides evidence that Aβ binds directly to α2 integrin in an integrin activation state dependent fashion.

2.3. α2 Knockout Mouse Cortical Cultures have Reduced Aβ Toxicity

Figure 3A:
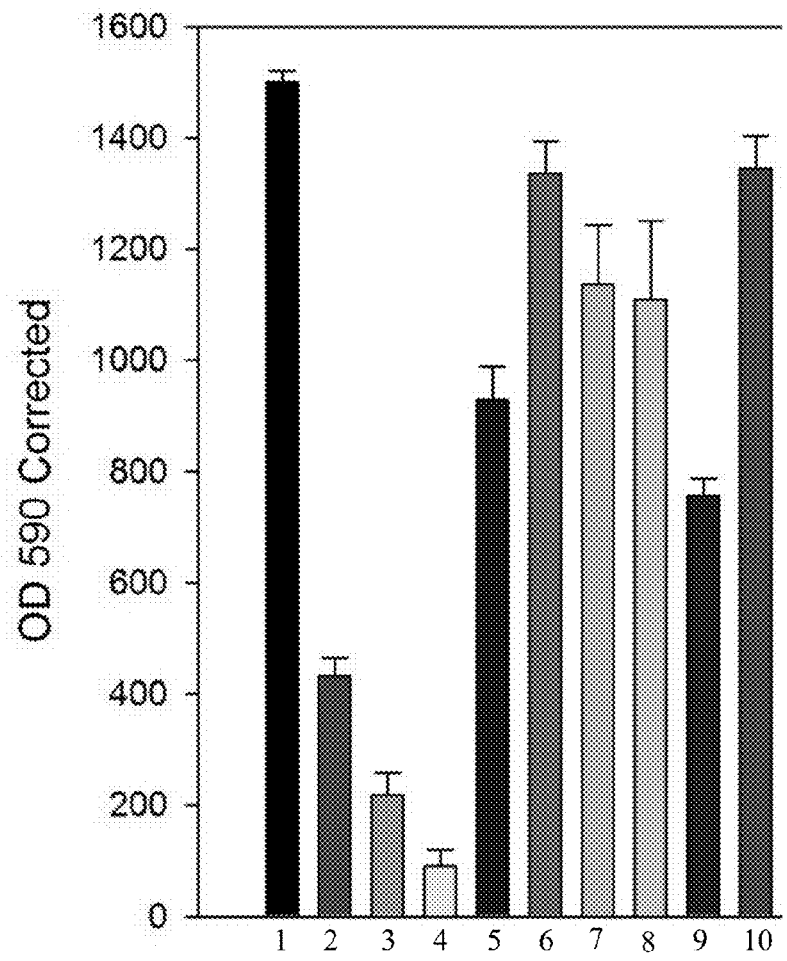
FIG. 3A: Aβ toxicity is decreased in mouse cortical cultures prepared from alpha 2 integrin null mice relative to wildtype mice.

Another way to show α2 integrin can mediate the toxicity was to prepare cortical cultures from wild-type mice and mice that lacked the alpha 2 integrin (alpha 2 null mice) (Chen et al. Am. J. Pathol. 161.1 (2002): 337-44). Cultures were then treated with Aβ and assayed for viability, FIG. 3A. All three doses of Aβ gave high toxicity (73% to 97% of control) in wild type cultures whereas in the α2 null cultures at the same doses gave much less toxicity (15 to 46% of control) This experiment again directly implicates α2 integrin as a mediator of the Aβ-induced toxicity.

2.4. Domain V's Protection from Aβ Neurotoxicity is α2 Integrin Dependent

Figure 3B:
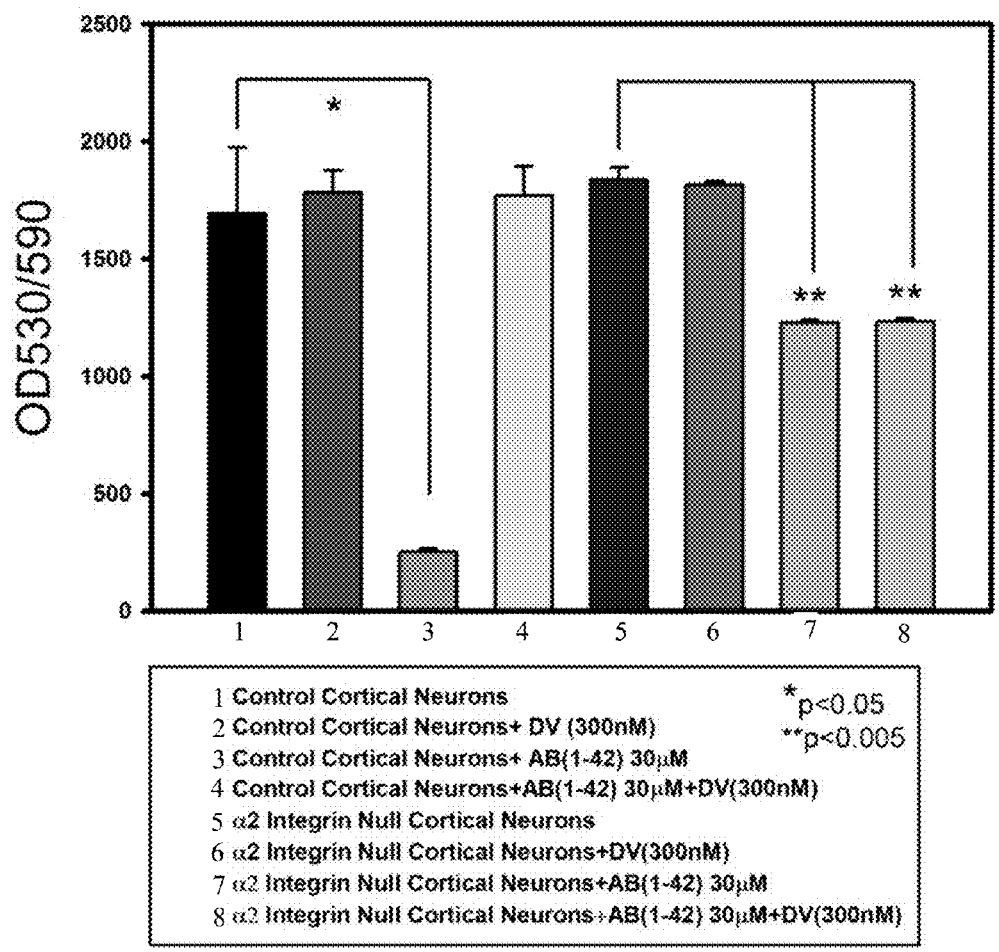
FIG. 3B: Domain V inhibits Aβ neurotoxicity in the α2 integrin cultures from wildtype mice without inhibiting residual Aβ neurotoxicity in the α2 integrin knockout mouse cultures.

To prove Aβ neurotoxicity is mediated through α2 integrin, α2 integrin wild type and knockout cultures were subjected to Aβ in the presence and absence of domain V and assayed for viability, FIG. 3B. Domain V protected from Aβ-mediated neurotoxicity but only in the α2 integrin wild type cultures, not in the α2 integrin knockout cultures, showing that domain V's neuroprotection is α2 integrin dependent. This experiment provides strong evidence that domain V protection from Aβ neurotoxicity is α2 integrin dependent.

Figure 4:
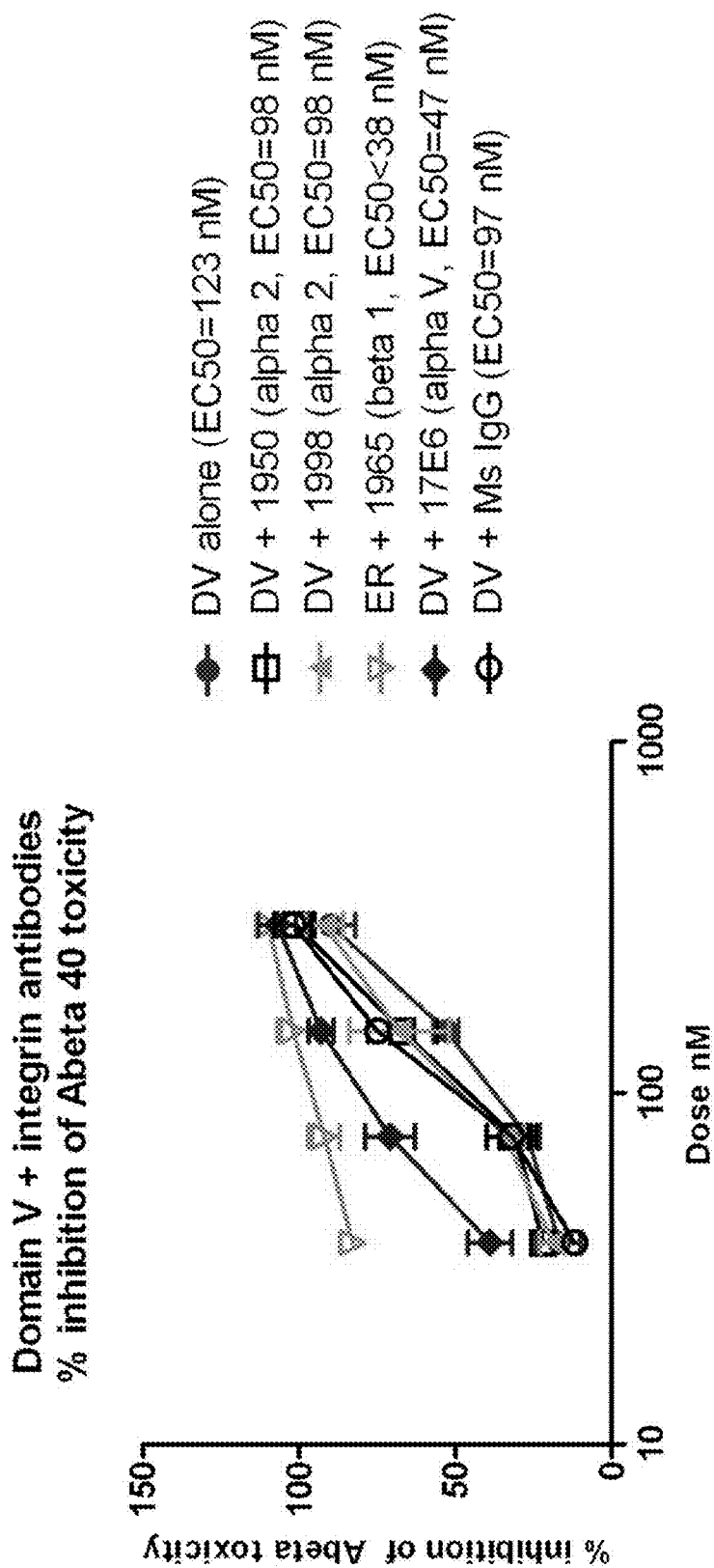
FIG. 4: Domain V inhibition of Aβ toxicity is enhanced by presence of αV and β1 integrin blocking antibodies but not α2 integrin blocking antibodies.

2.5. Domain V's Inhibition of Aβ Neurotoxicity is Potentiated with αV and β1 Antibodies Domain V was tested in Aβ neurotoxicity in combination with various integrin blocking antibodies to determine if they would act synergistically, have no effect, or whether they could block each other. Human cortical neurons were briefly pretreated with a dose response of domain V and then with Aβ mixed with one dose of integrin blocking antibody that by itself has little or no effect. FIG. 4 shows the titration of domain V inhibition of Aβ toxicity either by itself or with α2, αV or β1 blocking antibodies. Domain V alone inhibited Aβ toxicity with an EC50 of 123 nM (FIG. 4). In the presence of a mouse IgG control or the α2 antibodies 1950 and 1998, the EC50 of domain V was 98 nM. In the presence of the αV or β1 integrin antibodies, the EC50 of domain V markedly shifts to 47 nM and less than 38 nM, respectively. This result shows that αV and β1 blocking antibodies can act synergistically with domain V to inhibit Aβ toxicity, whereas the α2 antibodies have no effect.

2.6 Aβ Induced c-jun Activation is Inhibited by DV

Figure 7:
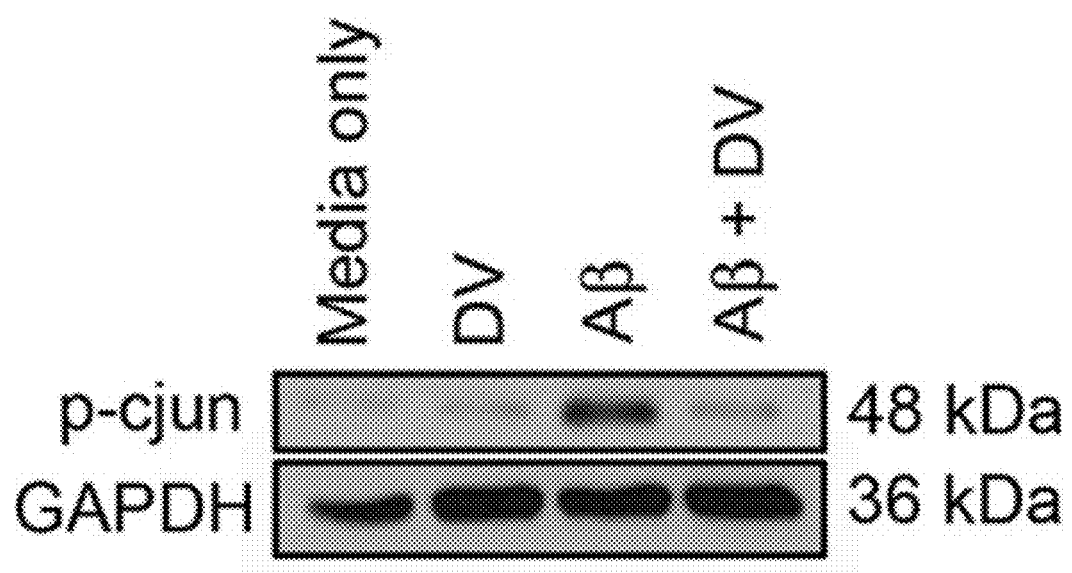
FIG. 7: Aβ-induced c-jun activation is inhibited by Domain V.

Aβ is known to induce the phosphorylation of c-jun in cortical neurons resulting in neurotoxicity. Wild-type MCC were treated with DV in the presence or absence of Aβ40 and c-jun phosphorylation was assessed by Western blot (FIG. 7). With Aβ treatment, c-jun phosphorylation was induced (upper band in blot) and this induction was inhibited in the presence of DV.

3. Discussion

The above experiments show domain V of perlecan inhibits both Aβ deposition onto neurons and its induced neurotoxicity in an α2 integrin dependent manner. The proteolytic fragment of DV that is responsible for the α2 integrin interaction, LG3, can also inhibit the Aβ deposition and toxicity. The experiments provide evidence that Aβ binds directly to α2 integrin to facilitate its deposition and induce neurotoxicity. It also places α2 integrin in a distinct pathway from αv integrin in the Aβ neurotoxicity pathway.

The signaling pathway that propagates the neurotoxic signal from Aβ is summarized in schematic form in FIG. 5 together with showing how domain V interferes with this pathway. Aβ binds to cells in an α2-dependent manner. This interaction, together with Aβ's interaction with αv integrin, initiates a chronically activated pathway through Pyk2 phosphorylation of paxillin. Subsequently, Tks5 is tyrosine phosphorylated leading to ADAM12's metalloprotease domain activation and cell death initiation through activation of JNK. Domain V or LG3 compete with Aβ for binding to α2 to inhibit the downstream pathway through Pyk2, Tks5, ADAM12 and JNK that induces neurotoxicity.

Example 2

One of the present inventors has shown that DV labeled with IR800 fluorescent dye targets diseased or damaged tissue in vivo, including tumors (Bix et al. (2006), J. Nat'l Cancer Inst. 98(22):1634-46) and stroked brain tissue (J. Neurochem. 104:55). In both cases, DV was found to deposit in a perivascular distribution, across the blood-brain barrier in the case of stroked tissue and into the tumor perivascular stroma in solid tumors. For the current experiments, IR800 fluorescently labeled DV (2 mg/kg dose) or IR800 dye alone was IP injected into PDAPP mice (a transgenic mouse characterized by an APP transgene with a FAD mutation at codon 717 and a β-PDGF promoter—see Games et al., supra) at an age at which plaques are beginning to deposit, around 12 months of age. PDAPP mice 18 months of age were also injected with IR800-labeled DV or dye alone. The injected mice were imaged at 6 hours, 24 hours, 3 days, 5 days, or 7 days post-injection with a Kodak small animal imager for real time pharmacokinetic analysis of administered DV distribution. The total pixel count in the head region was determined for each mouse. The results are shown in FIGS. 9A-C.

Figure 9A:
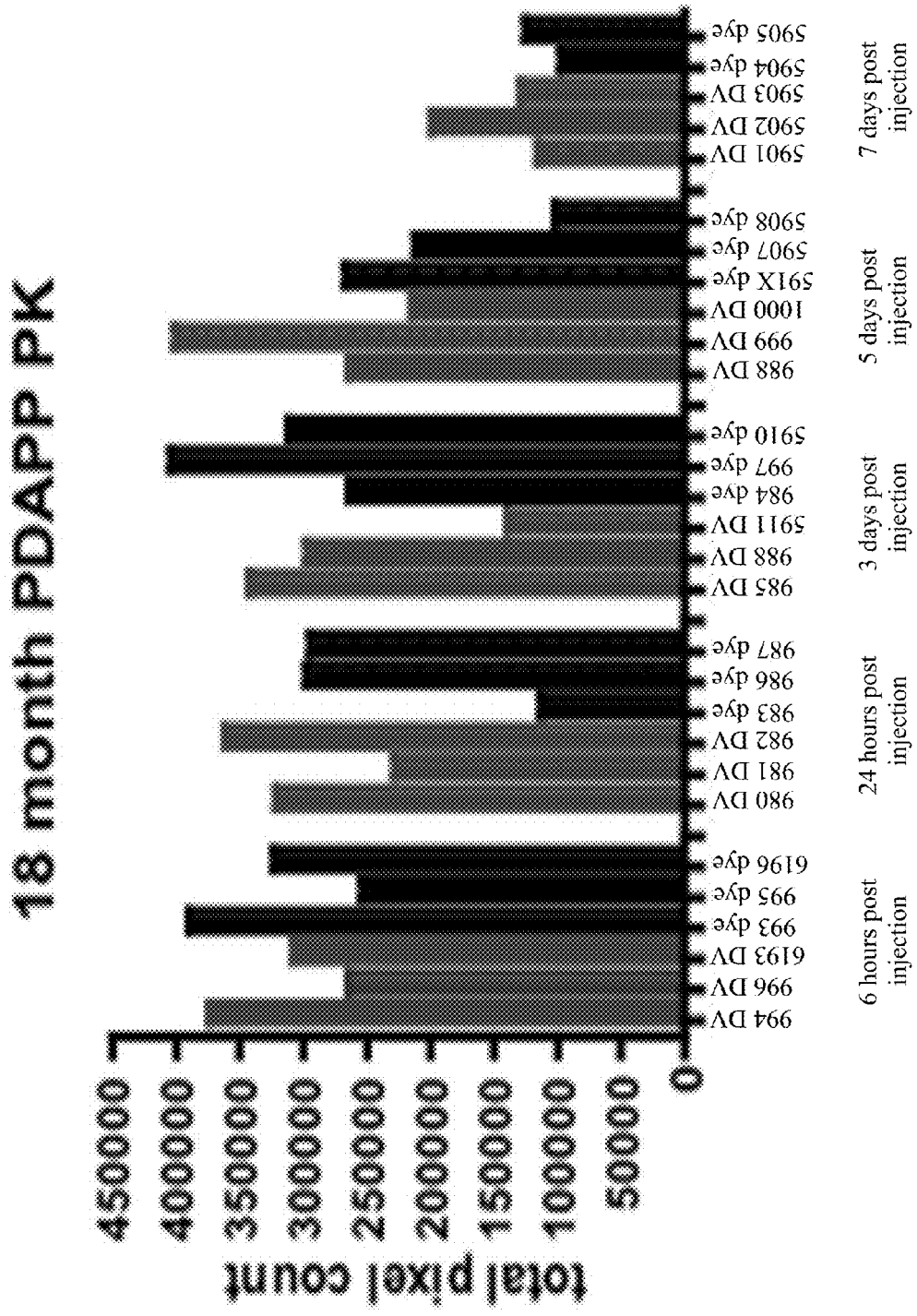
FIGS. 9A, B, and C: Pharmacokinetics of perlecan Domain V injected into mice. PDAPP mice were injected with IR800-dye conjugated DV and photographed with a Kodak In Vivo small animal imager at specific time points. The total pixel count in the head region was then quantitated and graphed for each mouse.
Figure 9B:
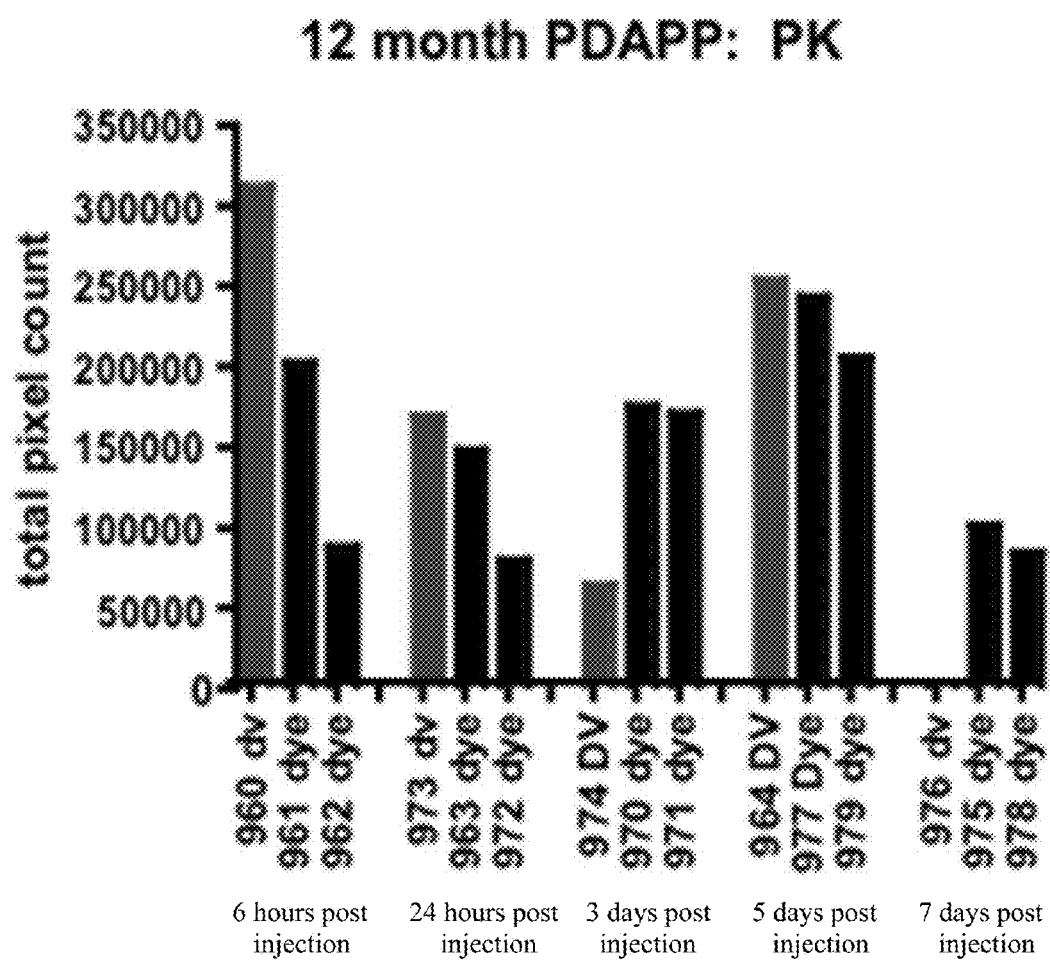
FIGS. 9B and 9C show the results for 12 month old mice. The mice in FIG. 9B were given a different preparation of dye conjugated DV than the mice in FIG. 9C.
Figure 9C:
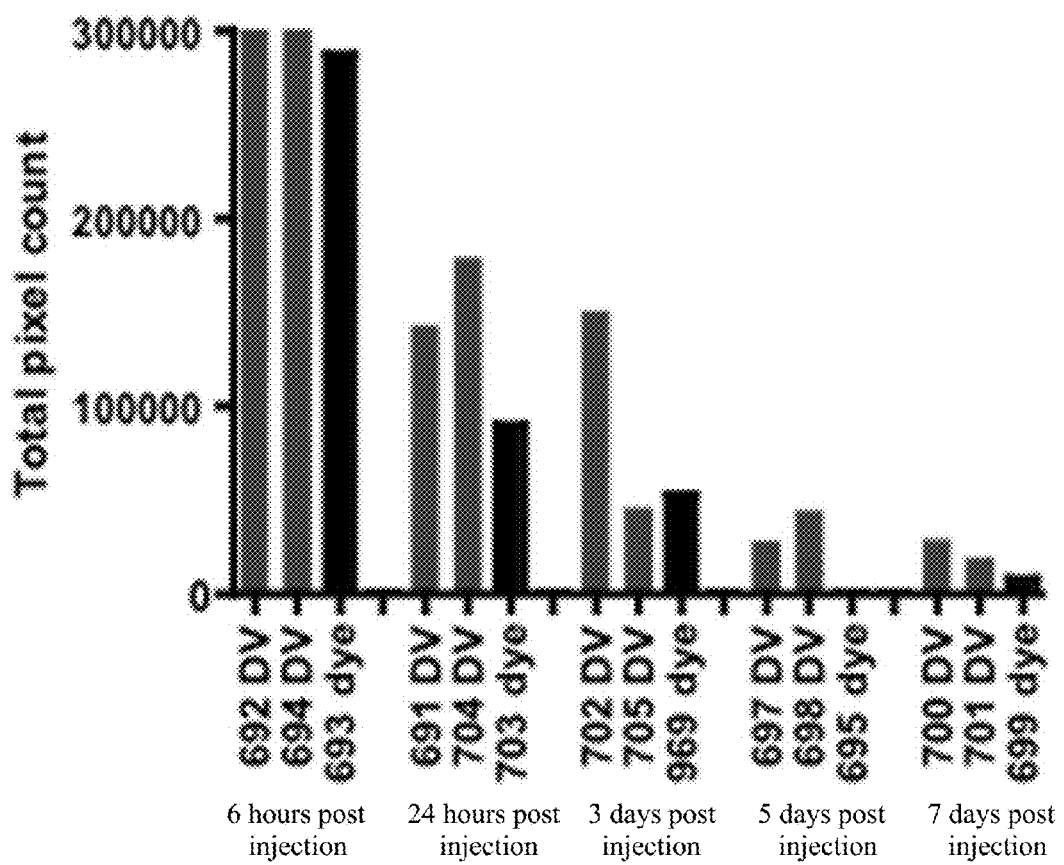

The results, as shown in FIGS. 9A-C, show no apparent difference in the pharmacokinetics of IR800-labeled DV and dye alone when injected into 12 and 18 month old PDAPP mice. The half-life of 1R800-labeled DV in 18 month old PDAPP mice appears to be longer than in 12 month old PDAPP mice, suggesting that receptor-mediated transfer across the blood-brain barrier is occurring in the 18 month old mice.

For further pharmacokinetic analysis, DV can be injected at several doses in a small number of animals and blood collected over a time course. The blood is assayed for presence of DV by Western blot (directed against the polyhistidine tag of the administered DV to distinguish it from endogenous DV). The animals are perfused and the brains removed and similarly assayed for DV by Western blot. Comparison of blood and brain levels gives a brain:plasma ratio, as well as information about how long the DV remains intact after treatment and guide the treatment paradigm for amount and timing of dosing.

In addition, DV or control protein is IP injected into PDAPP mice at 30 mice/group at an age at which plaques will just be beginning to deposit. The number of injections/week can vary (e.g., one injection every 5 days or an alternative frequency depending on the half-life determined in the previous experiment). This study runs for 6 months. Aβ is measured by ELISA in cortex and hippocampus and plaque levels determined by histology. DV can be of human or mouse origin, among others.

All patent filings, other publications, accession numbers and the like cited above are incorporated by reference in their entirety for all purposes to the same extent as if each individual item were specifically and individually indicated to be so incorporated by reference. If different variants of an a sequence are associated with an accession number at different times, the version associated with the accession number as of the effective filing date of this application (Jan. 6, 2010) is meant. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

What is claimed is:

1. A method of treating an amyloidogenic disease, the method comprising administering to a patient having the disease an effective regime of a fragment of perlecan optionally linked to a carrier, wherein the fragment of perlecan consists of:
   a) a polypeptide of SEQ ID NO:1 or a peptide having at least 95% sequence identity to SEQ ID NO:1; or
   b) a polypeptide of SEQ ID NO:5 or a peptide having at least 95% sequence identity to SEQ ID NO:5.

2. The method of claim 1, wherein the fragment of perlecan is linked to a carrier to facilitate passage across the blood brain barrier.

3. The method of claim 1, wherein the disease is type II diabetes, Parkinson's disease, prion infection, hereditary or systemic amyloidosis, Alzheimer's disease, Down's syndrome or mild cognitive impairment.

4. The method of claim 1, wherein the fragment of perlecan is selected from the group consisting of:
   a) the peptide consisting of the sequence of SEQ ID NO:1; and
   b) the peptide consisting of the sequence of SEQ ID NO:5.

5. The method of claim 1, the method further comprising administering an effective regime of an antibody to αv or β1 integrin.

6. The method of claim 5, wherein the antibody inhibits adhesion of αv integrin expressing cells to vitronectin, fibronectin or osteopontin or the antibody inhibits adhesion of β1 integrin expressing cells to fibronectin.

7. The method of claim 5, wherein the antibody is a monoclonal antibody.

8. The method of claim 7, wherein the monoclonal antibody:
   a) recognizes the same epitope as an antibody selected from 1965, Lia1/2, Gi9, 1950Z, VNR147, or 1980;
   b) is 1965, Lia1/2, Gi9, 1950Z, VNR147, or 1980; and
   c) competes for binding to αvβ1 with an antibody selected from among 1965, Lia1/2, Gi9, 1950Z, VNR147, and 1980.

9. A method of treating an amyloidogenic disease, comprising administering to a patient having the disease an effective regime of a fragment of perlecan or a fragment of perlecan that is linked to a carrier, said fragment of perlecan consisting of:
   a) perlecan domain V (SEQ ID NO:1);
   b) a peptide having at least 95% sequence identity to SEQ ID NO:1;
   c) SEQ ID NO: 5 (the LG3 domain of perlecan domain V); or
   d) a peptide having at least 95% sequence identity to SEQ ID NO:5.

10. The method of claim 9, wherein the disease is type II diabetes, Parkinson's disease, prion infection, hereditary or systemic amyloidosis, Alzheimer's disease, Down's syndrome or mild cognitive impairment.

11. The method of claim 9, wherein the fragment of perlecan further comprises a carrier linked to the fragment of perlecan to facilitate passage across the blood brain barrier.

12. The method of claim 11, wherein the carrier is a tat peptide.

13. The method of claim 9, the method further comprising administering an effective regime of an antibody to αv or β1 integrin.

14. The method of claim 13, wherein the antibody inhibits adhesion of αv integrin expressing cells to vitronectin, fibronectin or osteopontin or the antibody inhibits adhesion of β1 integrin expressing cells to fibronectin.

15. The method of claim 13, wherein the antibody is a monoclonal antibody.

16. The method of claim 15, wherein the antibody:
a) recognizes the same epitope as an antibody selected from 1965, Lia1/2, Gi9, 1950Z, VNR147, or 1980;
b) is 1965, Lia1/2, Gi9, 1950Z, VNR147, or 1980; and
c) competes for binding to αvβ1 with an antibody selected from among 1965, Lia1/2, Gig, 1950Z, VNR147, and 1980.

17. The method of claim 15, wherein the antibody is a human antibody or a humanized antibody.

18. The method of claim 9, wherein said fragment of perlecan consists of a peptide having at least 95% sequence identity to perlecan domain V (SEQ ID NO:1).

19. The method of claim 9, wherein said fragment of perlecan consists of the LG3 domain of perlecan domain V (SEQ ID NO:5).

20. The method of claim 9, wherein said fragment of perlecan consists of a peptide having at least 95% sequence identity to SEQ ID NO:5.

21. The method of claim 9, wherein said fragment of perlecan consists of perlecan domain V (SEQ ID NO:1).

22. A method of inhibiting Aβ-mediated toxicity in cells, comprising contacting the cells with a fragment of perlecan or a fragment of perlecan that is linked to a carrier, said fragment of perlecan consisting of:
a) perlecan domain V (SEQ ID NO:1); or
b) a peptide having at least 95% sequence identity to SEQ ID NO:1;
c) SEQ ID NO: 5 (the LG3 domain of perlecan domain V); or
d) a peptide having at least 95% sequence identity to SEQ ID NO:5.

23. The method of claim 22, wherein the contacting occurs in vitro.

24. The method of claim 22, wherein the contacting occurs in a subject.

25. The method of claim 24, wherein the subject is human.

26. The method of claim 24, wherein the subject is a transgenic animal model of Alzheimer's disease.

* * * * *

SEQUENCE LISTING

<160> NUMBER OF SEQ ID NOS: 9

<210> SEQ ID NO 1
<211> LENGTH: 729
<212> TYPE: PRT
<213> ORGANISM: Homo Sapiens

<400> SEQUENCE: 1

```
Val Pro Tyr Phe Thr Gln Thr Pro Tyr Ser Phe Leu Pro Leu Pro Thr
  1               5                  10                  15

Ile Lys Asp Ala Tyr Arg Lys Phe Glu Ile Lys Ile Thr Phe Arg Pro
             20                  25                  30

Asp Ser Ala Asp Gly Met Leu Leu Tyr Asn Gly Gln Lys Arg Val Pro
         35                  40                  45

Gly Ser Pro Thr Asn Leu Ala Asn Arg Gln Pro Asp Phe Ile Ser Phe
     50                  55                  60

Gly Leu Val Gly Gly Arg Pro Glu Phe Arg Phe Asp Ala Gly Ser Gly
 65                  70                  75                  80

Met Ala Thr Ile Arg His Pro Thr Pro Leu Ala Leu Gly His Phe His
                 85                  90                  95

Thr Val Thr Leu Leu Arg Ser Leu Thr Gln Gly Ser Leu Ile Val Gly
            100                 105                 110

Asp Leu Ala Pro Val Asn Gly Thr Ser Gln Gly Lys Phe Gln Gly Leu
        115                 120                 125

Asp Leu Asn Glu Glu Leu Tyr Leu Gly Gly Tyr Pro Asp Tyr Gly Ala
    130                 135                 140

Ile Pro Lys Ala Gly Leu Ser Ser Gly Phe Ile Gly Cys Val Arg Glu
145                 150                 155                 160

Leu Arg Ile Gln Gly Glu Glu Ile Val Phe His Asp Leu Asn Leu Thr
                165                 170                 175

Ala His Gly Ile Ser His Cys Pro Thr Cys Arg Asp Arg Pro Cys Gln
            180                 185                 190

Asn Gly Gly Gln Cys His Asp Ser Glu Ser Ser Ser Tyr Val Cys Val
        195                 200                 205

Cys Pro Ala Gly Phe Thr Gly Ser Arg Cys Glu His Ser Gln Ala Leu
    210                 215                 220

His Cys His Pro Glu Ala Cys Gly Pro Asp Ala Thr Cys Val Asn Arg
225                 230                 235                 240

Pro Asp Gly Arg Gly Tyr Thr Cys Arg Cys His Leu Gly Arg Ser Gly
                245                 250                 255

Leu Arg Cys Glu Glu Gly Val Thr Val Thr Thr Pro Ser Leu Ser Gly
            260                 265                 270

Ala Gly Ser Tyr Leu Ala Leu Pro Ala Leu Thr Asn Thr His His Glu
        275                 280                 285

Leu Arg Leu Asp Val Glu Phe Lys Pro Leu Ala Pro Asp Gly Val Leu
    290                 295                 300

Leu Phe Ser Gly Gly Lys Ser Gly Pro Val Glu Asp Phe Val Ser Leu
305                 310                 315                 320

Ala Met Val Gly Gly His Leu Glu Phe Arg Tyr Glu Leu Gly Ser Gly
                325                 330                 335
```

Leu Ala Val Leu Arg Ser Ala Glu Pro Leu Ala Leu Gly Arg Trp His
            340                 345                 350

Arg Val Ser Ala Glu Arg Leu Asn Lys Asp Gly Ser Leu Arg Val Asn
        355                 360                 365

Gly Gly Arg Pro Val Leu Arg Ser Ser Pro Gly Lys Ser Gln Gly Leu
    370                 375                 380

Asn Leu His Thr Leu Leu Tyr Leu Gly Gly Val Glu Pro Ser Val Pro
385                 390                 395                 400

Leu Ser Pro Ala Thr Asn Met Ser Ala His Phe Arg Gly Cys Val Gly
                405                 410                 415

Glu Val Ser Val Asn Gly Lys Arg Leu Asp Leu Thr Tyr Ser Phe Leu
            420                 425                 430

Gly Ser Gln Gly Ile Gly Gln Cys Tyr Asp Ser Ser Pro Cys Glu Arg
        435                 440                 445

Gln Pro Cys Gln His Gly Ala Thr Cys Met Pro Ala Gly Glu Tyr Glu
    450                 455                 460

Phe Gln Cys Leu Cys Arg Asp Gly Phe Lys Gly Asp Leu Cys Glu His
465                 470                 475                 480

Glu Glu Asn Pro Cys Gln Leu Arg Glu Pro Cys Leu His Gly Gly Thr
                485                 490                 495

Cys Gln Gly Thr Arg Cys Leu Cys Leu Pro Gly Phe Ser Gly Pro Arg
            500                 505                 510

Cys Gln Gln Gly Ser Gly His Gly Ile Ala Glu Ser Asp Trp His Leu
        515                 520                 525

Glu Gly Ser Gly Gly Asn Asp Ala Pro Gly Gln Tyr Gly Ala Tyr Phe
    530                 535                 540

His Asp Asp Gly Phe Leu Ala Phe Pro Gly His Val Phe Ser Arg Ser
545                 550                 555                 560

Leu Pro Glu Val Pro Glu Thr Ile Glu Leu Glu Val Arg Thr Ser Thr
                565                 570                 575

Ala Ser Gly Leu Leu Leu Trp Gln Gly Val Glu Val Gly Glu Ala Gly
            580                 585                 590

Gln Gly Lys Asp Phe Ile Ser Leu Gly Leu Gln Asp Gly His Leu Val
        595                 600                 605

Phe Arg Tyr Gln Leu Gly Ser Gly Glu Ala Arg Leu Val Ser Glu Asp
    610                 615                 620

Pro Ile Asn Asp Gly Glu Trp His Arg Val Thr Ala Leu Arg Glu Gly
625                 630                 635                 640

Arg Arg Gly Ser Ile Gln Val Asp Gly Glu Glu Leu Val Ser Gly Arg
                645                 650                 655

Ser Pro Gly Pro Asn Val Ala Val Asn Ala Lys Gly Ser Val Tyr Ile
            660                 665                 670

Gly Gly Ala Pro Asp Val Ala Thr Leu Thr Gly Gly Arg Phe Ser Ser
        675                 680                 685

Gly Ile Thr Gly Cys Val Lys Asn Leu Val Leu His Ser Ala Arg Pro
    690                 695                 700

Gly Ala Pro Pro Gln Pro Leu Asp Leu Gln His Arg Ala Gln Ala
705                 710                 715                 720

Gly Ala Asn Thr Arg Pro Cys Pro Ser
                725

<210> SEQ ID NO 2
<211> LENGTH: 42
<212> TYPE: PRT

```
<213> ORGANISM: Homo Sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 188
<212> TYPE: PRT
<213> ORGANISM: Homo Sapiens

<400> SEQUENCE: 3

Glu Arg Val Val Pro Tyr Phe Thr Gln Thr Pro Tyr Ser Phe Leu Pro
1               5                   10                  15

Leu Pro Thr Ile Lys Asp Ala Tyr Arg Lys Phe Glu Ile Lys Ile Thr
            20                  25                  30

Phe Arg Pro Asp Ser Ala Asp Gly Met Leu Leu Tyr Asn Gly Gln Lys
        35                  40                  45

Arg Val Pro Gly Ser Pro Thr Asn Leu Ala Asn Arg Gln Pro Asp Phe
    50                  55                  60

Ile Ser Phe Gly Leu Val Gly Gly Arg Pro Glu Phe Arg Phe Asp Ala
65                  70                  75                  80

Gly Ser Gly Met Ala Thr Ile Arg His Pro Thr Pro Leu Ala Leu Gly
                85                  90                  95

His Phe His Thr Val Thr Leu Leu Arg Ser Leu Thr Gln Gly Ser Leu
            100                 105                 110

Ile Val Gly Asp Leu Ala Pro Val Asn Gly Thr Ser Gln Gly Lys Phe
        115                 120                 125

Gln Gly Leu Asp Leu Asn Glu Glu Leu Tyr Leu Gly Gly Tyr Pro Asp
    130                 135                 140

Tyr Gly Ala Ile Pro Lys Ala Gly Leu Ser Ser Gly Phe Ile Gly Cys
145                 150                 155                 160

Val Arg Glu Leu Arg Ile Gln Gly Glu Glu Ile Val Phe His Asp Leu
                165                 170                 175

Asn Leu Thr Ala His Gly Ile Ser His Cys Pro Thr
            180                 185

<210> SEQ ID NO 4
<211> LENGTH: 182
<212> TYPE: PRT
<213> ORGANISM: Homo Sapiens

<400> SEQUENCE: 4

Thr Val Thr Thr Pro Ser Leu Ser Gly Ala Gly Ser Tyr Leu Ala Leu
1               5                   10                  15

Pro Ala Leu Thr Asn Thr His His Glu Leu Arg Leu Asp Val Glu Phe
            20                  25                  30

Lys Pro Leu Ala Pro Asp Gly Val Leu Leu Phe Ser Gly Gly Lys Ser
        35                  40                  45

Gly Pro Val Glu Asp Phe Val Ser Leu Ala Met Val Gly Gly His Leu
    50                  55                  60

Glu Phe Arg Tyr Glu Leu Gly Ser Gly Leu Ala Val Leu Arg Ser Ala
65                  70                  75                  80
```

Glu Pro Leu Ala Leu Gly Arg Trp His Arg Val Ser Ala Glu Arg Leu
                85                  90                  95

Asn Lys Asp Gly Ser Leu Arg Val Asn Gly Arg Pro Val Leu Arg
            100                 105                 110

Ser Ser Pro Gly Lys Ser Gln Gly Leu Asn Leu His Thr Leu Leu Tyr
            115                 120                 125

Leu Gly Gly Val Glu Pro Ser Val Pro Leu Ser Pro Ala Thr Asn Met
        130                 135                 140

Ser Ala His Phe Arg Gly Cys Val Gly Glu Val Ser Val Asn Gly Lys
145                 150                 155                 160

Arg Leu Asp Leu Thr Tyr Ser Phe Leu Gly Ser Gln Gly Ile Gly Gln
                165                 170                 175

Cys Tyr Asp Ser Ser Pro
            180

<210> SEQ ID NO 5
<211> LENGTH: 190
<212> TYPE: PRT
<213> ORGANISM: Homo Sapiens

<400> SEQUENCE: 5

Tyr Gly Ala Tyr Phe His Asp Asp Gly Phe Leu Ala Phe Pro Gly His
1               5                   10                  15

Val Phe Ser Arg Ser Leu Pro Glu Val Pro Glu Thr Ile Glu Leu Glu
                20                  25                  30

Val Arg Thr Ser Thr Ala Ser Gly Leu Leu Leu Trp Gln Gly Val Glu
            35                  40                  45

Val Gly Glu Ala Gly Gln Gly Lys Asp Phe Ile Ser Leu Gly Leu Gln
        50                  55                  60

Asp Gly His Leu Val Phe Arg Tyr Gln Leu Gly Ser Gly Glu Ala Arg
65                  70                  75                  80

Leu Val Ser Glu Asp Pro Ile Asn Asp Gly Trp His Arg Val Thr
                85                  90                  95

Ala Leu Arg Glu Gly Arg Arg Gly Ser Ile Gln Val Asp Gly Glu Glu
            100                 105                 110

Leu Val Ser Gly Arg Ser Pro Gly Pro Asn Val Ala Val Asn Ala Lys
        115                 120                 125

Gly Ser Val Tyr Ile Gly Gly Ala Pro Asp Val Ala Thr Leu Thr Gly
    130                 135                 140

Gly Arg Phe Ser Ser Gly Ile Thr Gly Cys Val Lys Asn Leu Val Leu
145                 150                 155                 160

His Ser Ala Arg Pro Gly Ala Pro Pro Gln Pro Leu Asp Leu Gln
                165                 170                 175

His Arg Ala Gln Ala Gly Ala Asn Thr Arg Pro Cys Pro Ser
            180                 185                 190

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
agggcgcgcc atcaagatca ccttccggc                              29

```
<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
agctcgagcc gaggggcagg ggcgtgtgtt g                              31

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
aggcatacgc atggcatagc aatagcagag tc                             32

<210> SEQ ID NO 9
<211> LENGTH: 32
<212> TYPE: DNA
<213> ORGANISM: Artificial Sequence
<220> FEATURE:
<223> OTHER INFORMATION: Primer

<400> SEQUENCE: 9
agctcgagca tgatgatgat gatgatgcga gg                             32
```